(12) United States Patent
Hillman

(10) Patent No.: US 10,045,688 B1
(45) Date of Patent: Aug. 14, 2018

(54) ACCESSORY FOR LARYNGOSCOPES, COMBINATION LARYNGOSCOPE AND ACCESSORY, AND/OR METHOD OF USING THE SAME

(71) Applicant: Beth Hillman, Park Ridge, IL (US)

(72) Inventor: Beth Hillman, Park Ridge, IL (US)

( * ) Notice: Subject to any disclaimer, the term of this patent is extended or adjusted under 35 U.S.C. 154(b) by 0 days.

(21) Appl. No.: 15/454,595

(22) Filed: Mar. 9, 2017

(51) Int. Cl.
*A61B 1/267* (2006.01)

(52) U.S. Cl.
CPC .................................. *A61B 1/267* (2013.01)

(58) Field of Classification Search
CPC ....................................................... A61B 1/267
USPC ................................ 600/186, 187, 190, 195
See application file for complete search history.

(56) References Cited

U.S. PATENT DOCUMENTS

| | | | | |
|---|---|---|---|---|
| 2,854,004 A | * | 9/1958 | Durrant | A61B 1/00094 600/187 |
| 4,126,127 A | * | 11/1978 | May | A61B 1/12 600/187 |
| 5,063,908 A | * | 11/1991 | Collins | A61B 1/32 128/DIG. 26 |
| 5,065,738 A | * | 11/1991 | Van Dam | A61B 1/00142 600/185 |
| 5,347,995 A | | 9/1994 | Slater | |
| 5,438,976 A | | 8/1995 | Nash | |
| 5,743,849 A | | 4/1998 | Rice | |
| 6,248,061 B1 | * | 6/2001 | Cook, Jr. | A61B 1/267 600/187 |
| 7,695,433 B2 | | 4/2010 | Simons | |
| 9,078,615 B2 | | 7/2015 | Young | |
| 2005/0240081 A1 | * | 10/2005 | Eliachar | A61B 1/267 600/199 |
| 2009/0294313 A1 | | 12/2009 | Pacey | |
| 2010/0121152 A1 | * | 5/2010 | Boedeker | A61B 1/00094 600/187 |
| 2010/0191061 A1 | | 7/2010 | Simons | |
| 2011/0092773 A1 | * | 4/2011 | Goldstein | A61B 1/015 600/187 |
| 2014/0296645 A1 | | 10/2014 | McGrath | |
| 2015/0305611 A1 | | 10/2015 | Young | |
| 2015/0351622 A1 | | 12/2015 | Nopasri | |

* cited by examiner

*Primary Examiner* — Pedro Philogene
*Assistant Examiner* — David C Comstock
(74) *Attorney, Agent, or Firm* — Garcia-Zamor IP Law; Ruy M. Garcia-Zamor

(57) ABSTRACT

An accessory for laryngoscopes configured for being detachably affixed to laryngoscopes, a combination laryngoscope and accessory, and/or methods of use of the accessory and/or combination laryngoscope and accessory. The accessory, combination laryngoscope and accessory, and/or method is preferably configured to increase comfort, safety, and the efficiency of use of laryngoscopes in the medical profession.

13 Claims, 15 Drawing Sheets

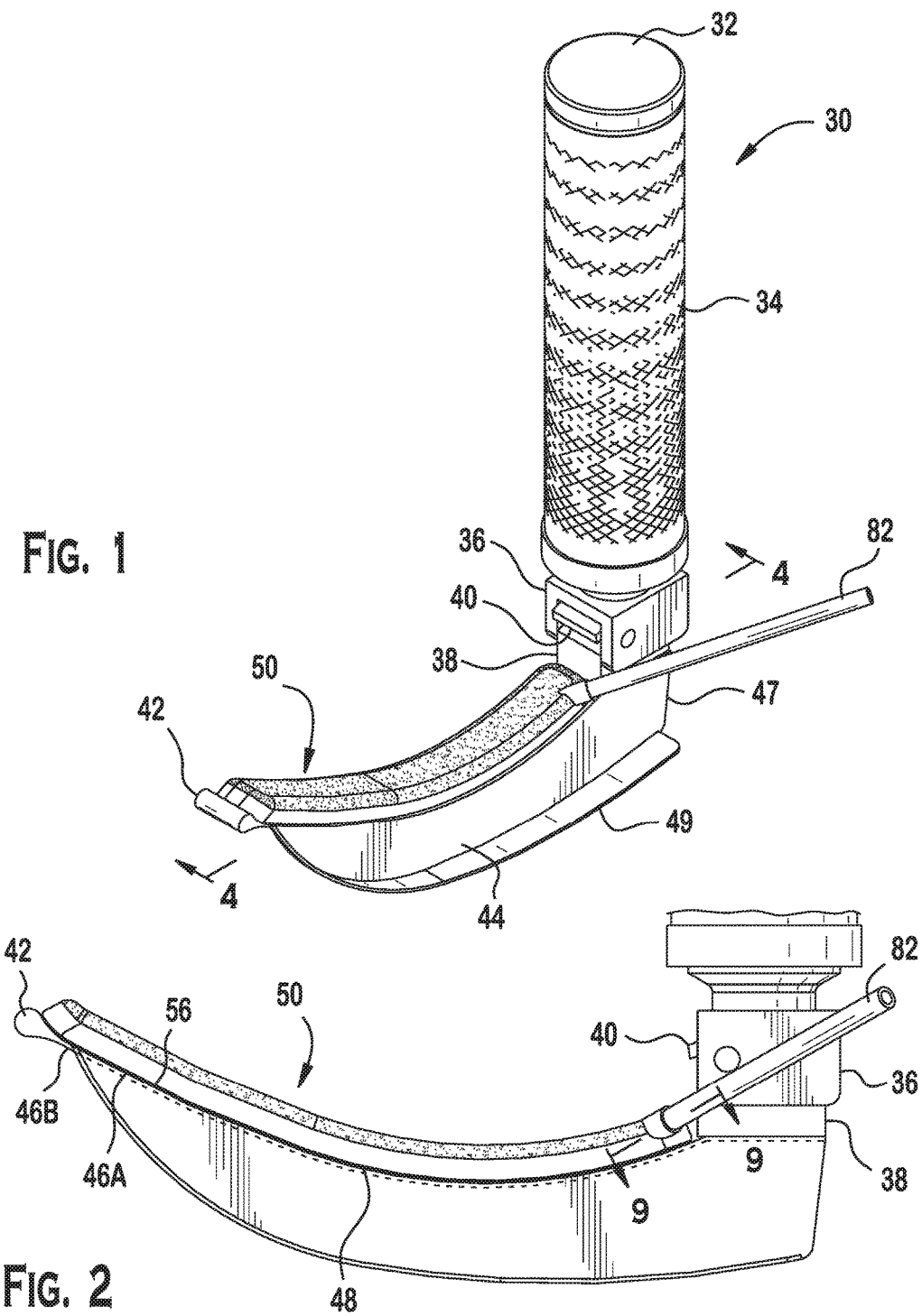

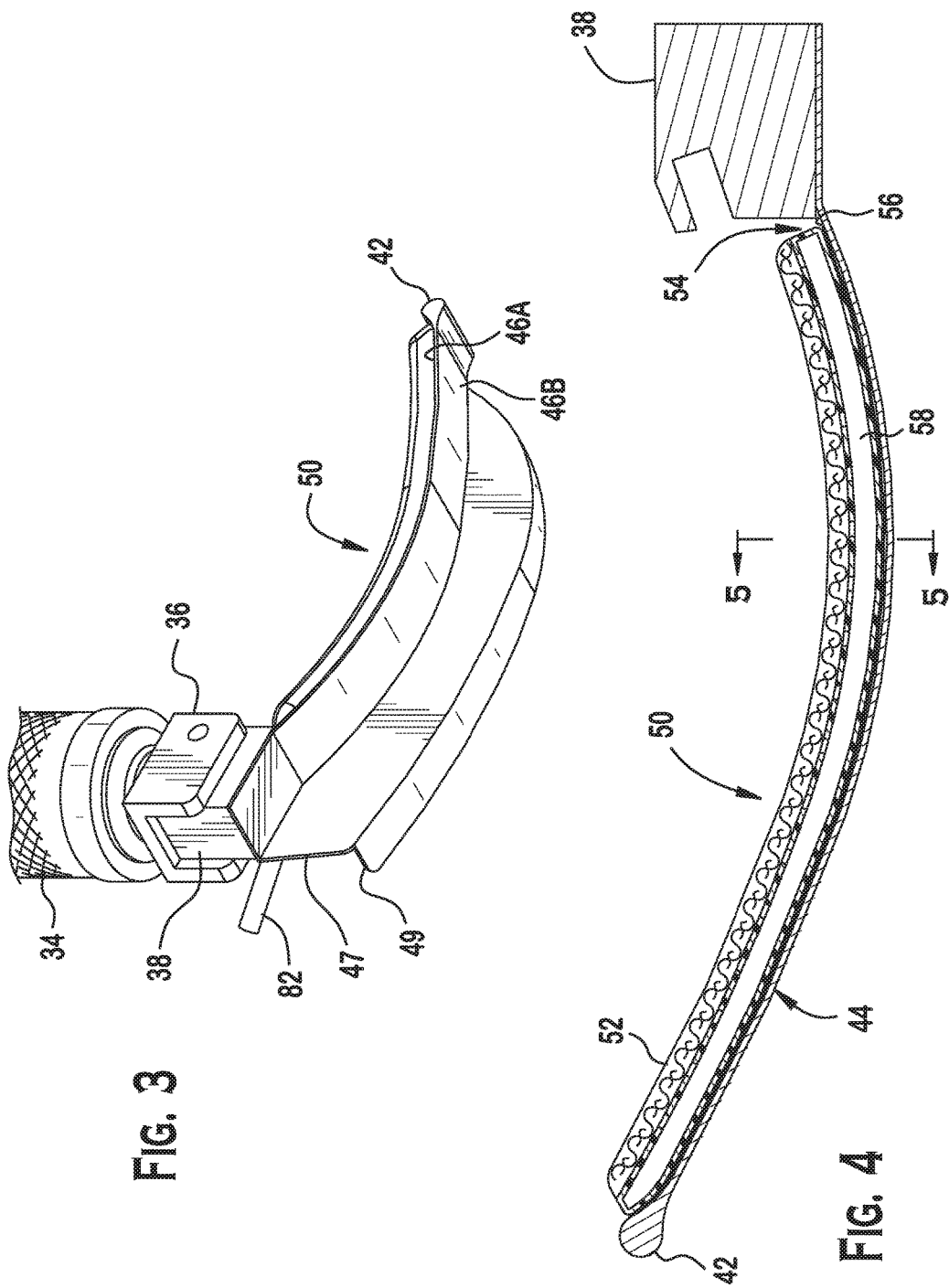

ACCESSORY FOR LARYNGOSCOPES, COMBINATION LARYNGOSCOPE AND ACCESSORY, AND/OR METHOD OF USING THE SAME

BACKGROUND

The present invention is directed to medical device accessories generally, and more specifically to accessories for laryngoscope blades.

Existing laryngoscope blades suffer from one or more of several existing deficiencies. Existing laryngoscopes require medical personnel to use the laryngoscope blade to move and hold the patient's tongue to one side during intubation. It can be difficult to hold the tongue to the side due to the presence of liquid in the mouth, including saliva or blood, which can cause the tongue to become slippery. Liquid in the mouth can also increase the difficulty in performing endotracheal intubation as the liquid may obstruct medical professionals' view of the vocal chords, prolonging the intubation process or preventing it altogether. Further, laryngoscope blades can also be damaging to patients' mouths, with the blade coming in contact with teeth or soft mouth tissue.

It may be advantageous to provide a method of properly configuring a patient for airway tube insertion, to provide an accessory for laryngoscopes, to provide a laryngoscope, or to provide a combination laryngoscope and accessory which: can be detachably affixed to a portion of the laryngoscope blade to provide an absorbent cover which increases grip and decreases moisture between the blade and a patient's tongue; that includes a vacuum element to remove liquid from the mouth without necessitating a large section of absorbency; which may be held to the laryngoscope blade by adhesive; which may use suction tubing as part of a safety retention device; which can be used with existing laryngoscopes, that is efficient to manufacture; and/or which results in greater patient care.

SUMMARY

Briefly speaking, one embodiment of the present invention is directed to an accessory configured for detachable placement on a blade of a laryngoscope. The blade having first and second opposing major blade surfaces. The accessory may include a container defining a chamber therein. The container has an upper surface and a lower surface. At least one channel is formed in an outer surface of the container such that liquid can enter the chamber. A tube defines a passageway therethrough and connects to the container. The passageway is in fluid communication with the chamber. A padding layer includes absorbent material and is located on the upper surface of the container. An adhesive layer is located on the lower surface of the container such that the accessory is configured to be temporarily affixed to the blade of the laryngoscope. The accessory is configured to only contact one of the first and second opposing major blade surfaces and to cover at least a portion thereof. The tube is configured to transfer a vacuum to the chamber such that liquid that enters the container, regardless of whether the liquid travels through the padding layer first, can be removed from the chamber via the passageway.

In a separate aspect, the present invention is directed to an accessory configured for detachable placement on a blade of a laryngoscope in which the accessory may be comprised of opposing sides, specifically an adhesive layer and absorbent layer. The two layers may define a container creating a chamber for liquid to enter and be removed from via a tube.

In a separate aspect, the present invention is directed to an accessory having a container that is flexible, to allow for the accessory to generally maintain its shape if suction is applied but to fit to curved or straight laryngoscope blades. In some aspects, the tube may be attached to a suction device to remove liquid which may seep through pores or openings in the absorbent layer.

In a separate aspect, the present invention is directed to an accessory including two tubes, one to push air into the chamber and a second to suck air and liquid from the chamber, creating a steady vacuum without collapsing the container.

BRIEF DESCRIPTION OF THE DRAWINGS

The foregoing summary, as well as the following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 1 is a front perspective view of a laryngoscope 30 with the accessory 50 attached, demonstrating that laryngoscopes 30 may include a laryngoscope handle 32 with grip 34 to facilitate handling and a bracket 36 into which a bracket insert 38 may be placed and locked into place by a bracket lock 40. The bracket insert 38 and bracket lock 40 may be affixed to laryngoscope blades 44 and may allow detachable blades 44 to be attached or removed from the same laryngoscope handle 32.

FIG. 2 is a partial front elevational view of a laryngoscope blade 44 with the accessory 50 attached, demonstrating that the laryngoscope blade 44 may include a blade tip 42 on one axial end and the bracket insert 38 on the other, and opposing first and second major blade surfaces 46A and 46B with the accessory 50 affixed to the first major blade surface 46A.

FIG. 3 is a partial rear perspective view of a laryngoscope blade 44 with the accessory 50 attached, demonstrating that the laryngoscope blade 44 may also include a guide flange 47 extending downward from a lateral side of the laryngoscope blade 44. A minor blade surface 48 may be formed of the opposing lateral side of the laryngoscope blade 44. The guide flange 47 may also include an abutment plate 49 extending radially from the guide flange 47.

FIG. 4 is a cross-sectional view of a portion of the laryngoscope and accessory of FIG. 1 as taken along the lines 4-4 of FIG. 1 demonstrating that the preferred embodiment of the accessory 50 may include a padding layer 52, a container 54 defining a chamber 58, and an adhesive layer 56 affixed to the first major blade surface 46A.

FIG. 13 is an alternative cross-sectional view of FIG. 12 wherein the support partitions 70 may extend from a single insert flange 69 which may formed of a separate piece than the container 54. This may allow the support partitions 70 to be formed of inflexible material while the upper surface 60 may be formed of flexible material, allowing for flexibility of the container 54 without jeopardizing the chamber 58 to allow liquid and/or air to pass there through.

FIG. 15 is a partial front perspective view of a preferred embodiment of the accessory with a portion cut-away for reference demonstrating the plurality of channels 64 which may be included in the container 54 and further demonstrating that the support partitions 70 may be roughly conical in shape to create more paths for liquid and/or air to travel through.

FIG. 17 is an alternative cross-sectional view of FIG. 16 wherein the support partitions 70 may extend from a single insert flange 69 which may formed of a separate piece than the container 54. This may allow the support partitions 70 to be formed of inflexible material while the upper surface 60 may be formed of flexible material, allowing for flexibility of the container 54 without jeopardizing the chamber 58 to allow liquid and/or air to pass there through.

DETAILED DESCRIPTION OF THE PREFERRED EMBODIMENT

Figure 6:
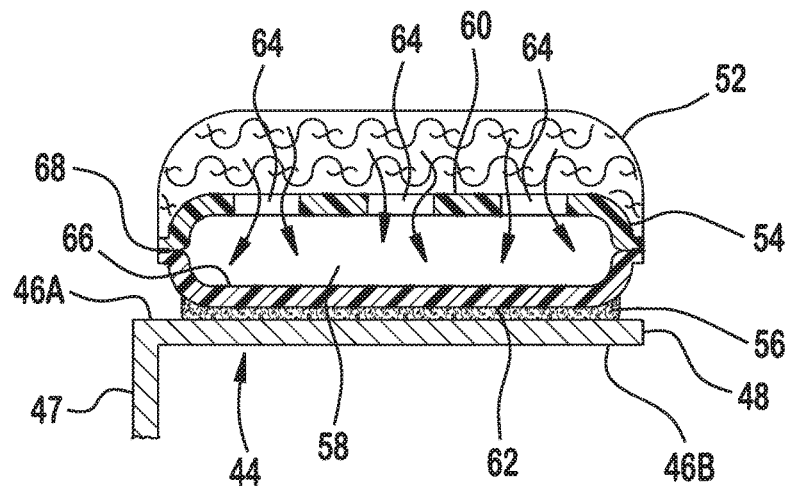
FIG. 6 is a cross-sectional view of a portion of an alternate embodiment of the laryngoscope and accessory of FIG. 5 demonstrating that in some preferred embodiments the connecting piece 68 may be formed by a seam created where the upper surface 60 and lower surface 62 meet.
Figure 7:
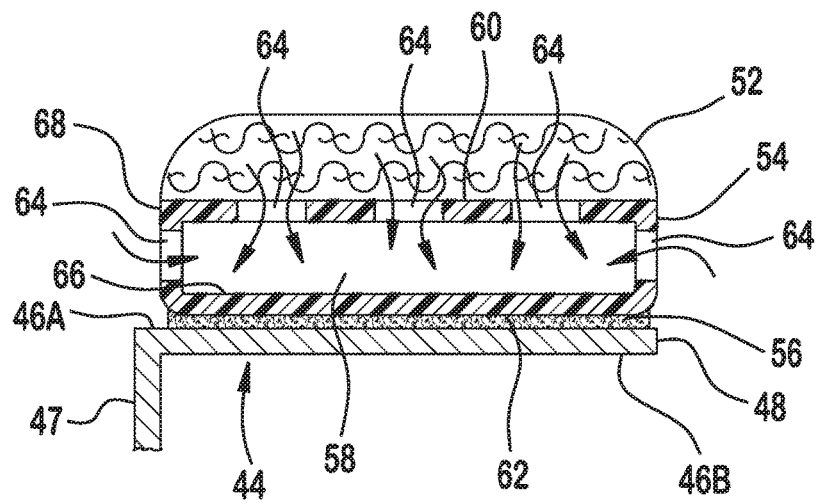
FIG. 7 is a cross-sectional view of a portion of an alternate embodiment of the laryngoscope and accessory of FIG. 5 demonstrating that in some preferred embodiments the connecting piece 68 may formed of a sidewall, and that at least one channel 64 may be include in the connecting piece 68 and/or the upper surface 60.
Figure 8:
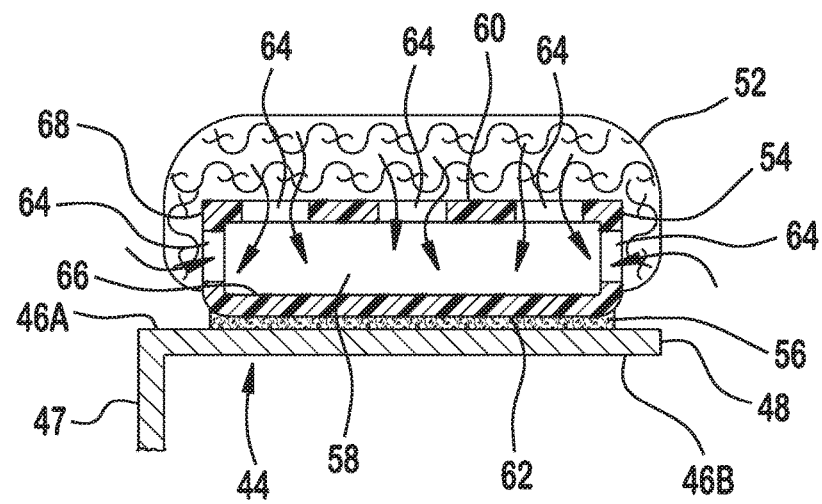
FIG. 8 is a cross-sectional view of a portion of an alternate embodiment of the laryngoscope and accessory of FIG. 7 demonstrating that in some preferred embodiments the padding layer 53 may cover the connecting piece 68. The connecting piece 68 may be covered in the place of the upper surface 60 or in addition to the upper surface 60.
Figure 9:
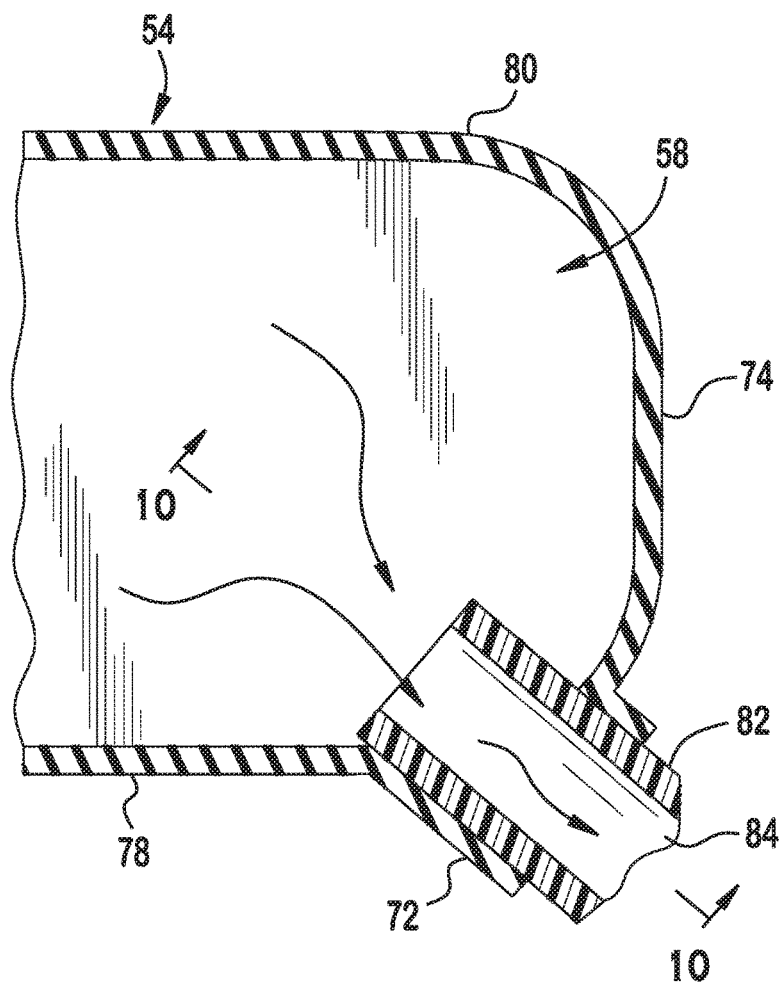
FIG. 9 is a schematic view of the portion of the accessory of FIG. 2 as taken along the lines 9-9 of FIG. 2 demonstrating that the container 54 may include first and second axial ends 74 and 76, and first and second lateral ends 78 and 80. The container 54 may also include a port 72 into which a tube 82 may be inserted to place a passageway 84 defined by the tube 82 in fluid connection with the chamber 58.
Figure 10:
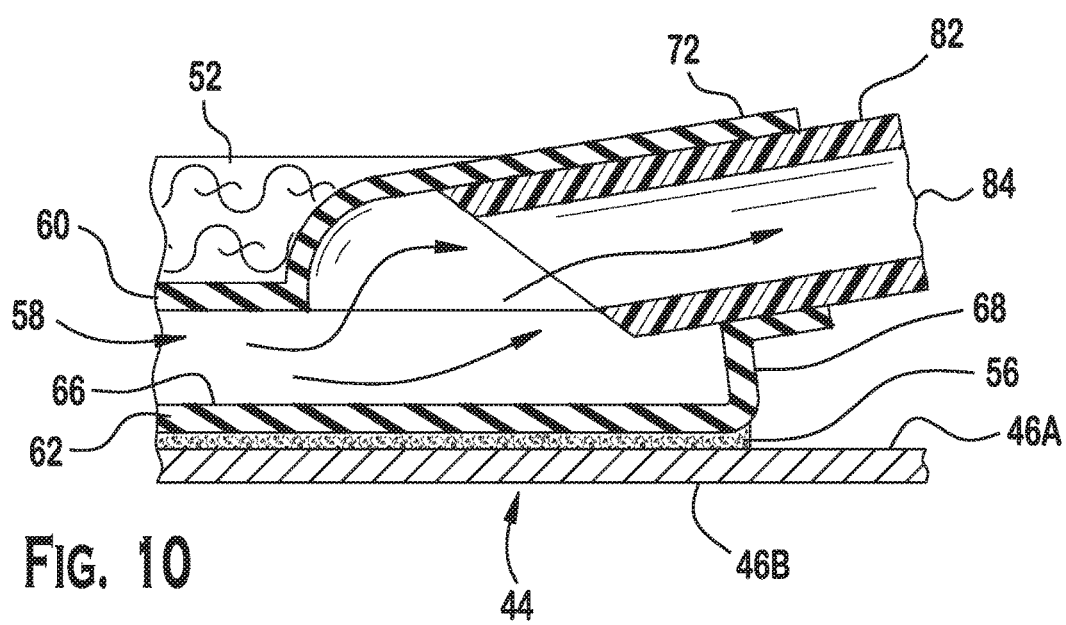
FIG. 10 is a cross-sectional schematic view of the portion of the accessory of FIG. 9 as taken along the lines 10-10 of FIG. 9 demonstrating that fluid and air may travel from the container 54 through the passageway 84 in the tube 82 if a suction device 86 is applied at the end of the tube 82.
Figure 11:
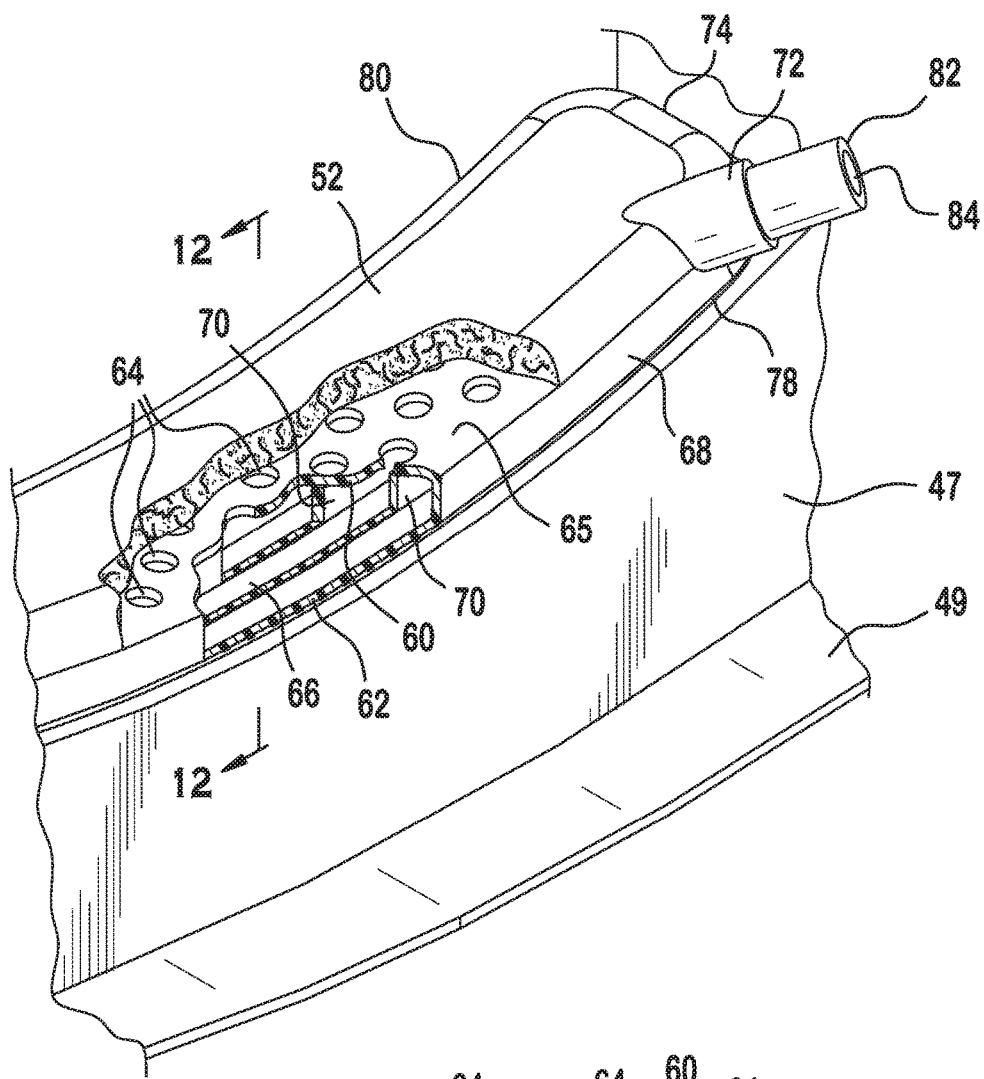
FIG. 11 is a partial front perspective view of a preferred embodiment of the accessory with a portion cut-away for reference demonstrating the plurality of channels 64 which may be included in the container 54 and how support partitions 70 may be included to separate the chamber 68 to allow liquid to travel along different paths while adding support to the container 54.
Figure 12:
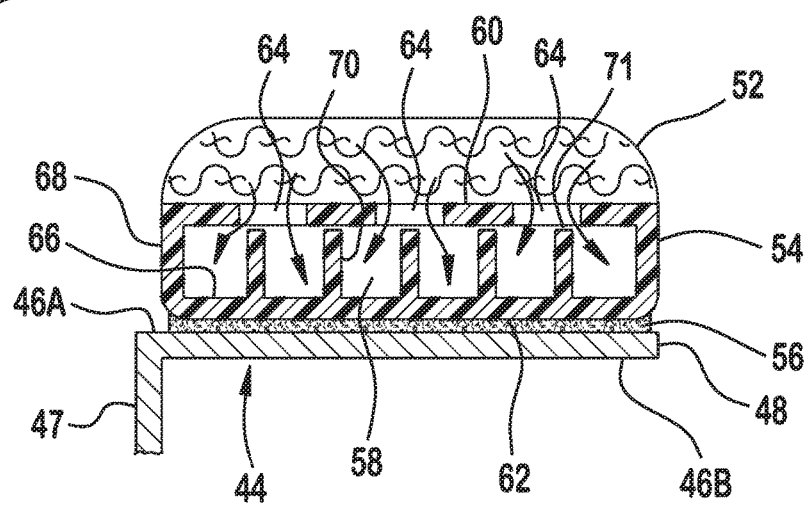
FIG. 12 is a cross-sectional view of a portion of the laryngoscope and accessory of FIG. 11 as taken along the lines 12-12 of FIG. 11 demonstrating that a gap 71 may be included between each support partition 70 and the upper surface 60 of the container 54. This may allow the container to flex while adding greater stability to the container 54, ensuring the chamber 58 is properly defined.

Certain terminology is used in the following description for convenience only and is not limiting. The words "right," "left," "top," and "bottom" designate directions in the drawings to which reference is made. In reference to the laryngoscope, the handle extends generally upward, as does the "inner side" of the laryngoscope blade. The words "outer" and "inner" refer to directions away from and toward, respectively, the geometric center of the accessory. The term "not generally planar parallel" designates surfaces in which a majority of the surface is positioned more than five degrees (5°) of true mathematic parallel from another surface. That is to say it refers to a surface that in reference to an imaginary stable line bisecting the surface, the surface extend away in an angle more than five degrees (5°) different than angle of a referenced other surface. The term "generally perpendicular" designates a surface in which a majority of the first referenced surface is positioned within thirty five degrees (35°) of true mathematic perpendicular from another referenced surface. Referring to FIG. 6, it is understood that the connecting piece 68 is not generally planar parallel to the first major blade surface 46A when the device is in use because only a small portion of the connecting piece 68 may be parallel to the first major blade surface 68A at any given time. Axial refers to positions along or parallel to a horizontal axis through the center of the laryngoscope blade when place such that the blade tip and bracket insert are on opposite horizontal sides. Radial refers to directions to positions along or parallel to a vertical axis through the center of the laryngoscope blade when place such that the blade tip and bracket insert are on opposite horizontal sides. When the term fluid is used, it may include liquids, solids or semi solids such as blood clots, chunks, and/or pieces of viscera, gasses and air. Additionally, the words "a" and "one" are defined as including one or more of the referenced item unless specifically stated otherwise. The terminology includes the words above specifically mentioned, derivatives thereof, and words of similar import.

Referring to FIGS. 1-28 wherein like numerals indicate like elements throughout, there are shown preferred embodiments of an accessory 50 for laryngoscopes 30. The accessory 50 is preferably, but not necessarily, configured to be detachably affixed to laryngoscope blades 44 prior to each use with patients. Arrows in the figures demonstrate potential paths for water and/or air to take when moving through the accessory 50.

Referring to FIGS. 1-3, laryngoscopes 30 are generally configured to have detachable laryngoscope blades 44. These laryngoscopes 30 preferably comprises a laryngoscope handle 32 which may be overlaid with or textured with a grip 34 to make handling the laryngoscope 30 easier when the handle 32 is wet. The handle 32 may include a bracket 36 into which a bracket insert 38 may be inserted and locked into place with a lock 40. Preferably, the bracket 36 is present at the end of the handle 32 to allow for the laryngoscope 30 form a rough sickle shape. The bracket insert 38 is preferably affixed to a laryngoscope blade 44 at the opposite axial end of the laryngoscope blade 44 than a blunt blade tip 42. However, in some preferred embodiments the laryngoscope 30 may include a handle ending in the laryngoscope 44, with the blade 44 being permanently attached to the handle 32 directly.

The laryngoscope blade 44 may preferably include first and second opposing major blade surfaces 46A and 46B. The first major blade surface 46A may be the inner curve of the blade 44 which faces upwards, while the second major blade surface 46B may be the outer curve of the blade 44 which faces downward. The laryngoscope blade 44 may also include minor blade surfaces 48 between the major blade surfaces 46 if the major blade surfaces 46 do not meet at a seam. In the preferred in embodiment, a minor blade surface 48 may be include at the end of the major blade surfaces 46, opposite of a guide flange 47. A guide flange 47 may be a structure which extends radially downward from the laryngoscope blade 44 to provide a surface along which the user may slide an intubation tube into a patient's throat. The guide flange 47 may be flat, curved, or provided in any other shape which may allow assist the user. In some embodiments, the guide flange 47 may end in an abutment plate 49 being roughly parallel to the guide flange 47 to further facilitate intubation.

Laryngoscope blades 44 may be provided in varying shapes and sizes. Laryngoscope blades 44 may be straight, such as McGill or Miller blades, or curved, such as Macintosh blades. Laryngoscope blades 44 may be sized specifically for certain patients, being smaller for children and larger for adults. Laryngoscopes 30 may be configured for use with detachable blades, or the blades may be permanently affixed. The laryngoscope 40 depicted in the drawings is comprised of a curved laryngoscope blade 44 sized for use with adult patients, with the accessory 50 sized accordingly. However, those of ordinary skill in the art may appreciate from this disclosure that the accessory 50 may be provided for use with laryngoscopes 30 of varying shapes and sizes, without claim to particular shapes and sizes without departing from the scope of this disclosure. The laryngoscope 30 may be configured to include detachable blades 44 which may be replaced with blades of other shapes and sizes. Conversely, the laryngoscope 30 may be comprised of a single handle 32 and a single blade 44. Those of ordinary skill in the art will appreciate from this disclosure that laryngoscopes 30 may be comprised of non-detachable blades 44 without departing from the scope of the present invention. Those of ordinary skill in the art will further appreciate from this disclosure that the accessory 50 may be used on laryngoscope blades 44 without a minor blade surface 48, bracket 36, or bracket insert 38 without departing from the scope of the present invention, such as blades in which the major blades surfaces 46 meet in a single point or which extend axially directly from the laryngoscope handle 32. Preferably, the accessory 50 may be affixed to the first major blade surface 46 and may at least of portion of the first major blade surface 46. The accessory 50 may be configured such that it does not cover any portion of the second major blade surface 48. The accessory 50 preferably covers all of the first major blade surface 46 without covering a significant portion of non-major blade surfaces. However those of ordinary skill in the art will appreciate from this disclosure that the accessory 50 may cover portions of non-major blade surfaces without departing from the scope of the present invention. Further, those of ordinary skill in the art will appreciate from this disclosure that the accessory 50 may leave a portions of the first major blade surface 46 uncovered without departing from the scope of the present invention.

The laryngoscope 30, which may include the laryngoscope blade 44, handle 32, bracket 36, bracket insert 38, and lock 40, is preferably formed of the same material. Preferably the laryngoscope 30 is formed of a hard material which can be exposed to liquid, such as stainless steel or molded plastic. Preferably, the grip 34 may be texture added to the handle 32 and so may be formed of the same material as the handle 32. In other preferred embodiments, the grip 34 may be formed of rubber, tactile plastic, or any other suitable material which may increase grip on the handle 32. Those of ordinary skill in the art will appreciate from this disclosure that the laryngoscope 30 may be formed of any suitable material without departing from the scope of the present invention. Further, those of ordinary skill in the art will appreciate from this disclosure that the some parts of the laryngoscope 30 may be formed of different materials than some other parts of the laryngoscope 30 without departing from the scope of the present invention.

Figure 5:
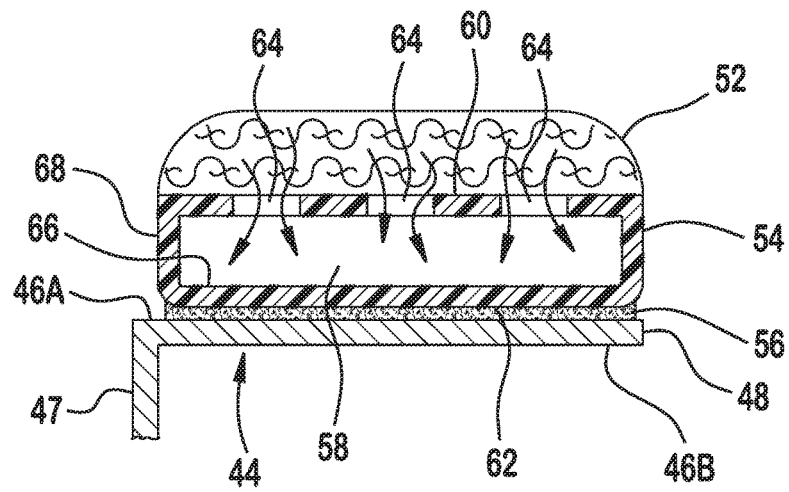
FIG. 5 is a cross-sectional view of a portion of the laryngoscope and accessory of FIG. 4 as taken along the lines 5-5 of FIG. 4 demonstrating that the container 54 may include an upper surface 60, a lower surface 65, and a connecting piece 68 connecting the two. These surfaces 60, 65, and 68 may define an outer surface of the container 65 with at least one channel 64 there through, which may place the inner surface 66 of the container 54 in connection with the air outside of the container 54. In the preferred embodiment, the padding layer 52 may be affixed to the upper surface 60 and the adhesive layer 56 may be affixed to the lower surface, with the channels 64 preferably being present in the upper surface 60.

Referring to FIGS. 4 and 5, the accessory 50 may preferably include a padding layer 52, an adhesive layer 56 affixing the accessory 40 to first major blade surface 46, and a container 54. The container may define a chamber 58 therein, and may include an upper surface 60, a lower surface 62, at least one channel 64 in the outer surface 65 of the container 54 such that liquid can enter the chamber 58, and a tube 82 in fluid communication with the chamber 58. In the preferred embodiment, the padding layer 52 may be formed of a single section of padding, the adhesive layer 56 may be formed of a single section of adhesive, and the accessory 50 include a single container 54 and a single chamber 58. Those of ordinary skill in the art will appreciate from this disclosure that the padding layer 52 and adhesive layer 56 may be formed of more than one sections of non-connected padding or non-connected adhesive respectively without departing from the scope of the present invention. Those of ordinary skill in the art will further appreciate from this disclosure that the accessory 50 may comprise more than one non-connected container 54 and/or more than one chamber 58 without departing from the scope of the present invention. Those of ordinary skill in the art will also appreciate from this disclosure that the adhesive layer 56, padding layer 52, and/or the container 54 may cover only a portion of the laryngoscope blade 44 without departing from the scope of the present invention.

Referring to FIGS. 4-8 and 11-13, the padding layer 52 is preferably located on the upper surface 60 of the container 54. The passing layer 52 may be formed of absorbent, permeable or semi-permeable material. Such a material may allows liquid to pass through the padding layer 52 while also padding the first major blade surface 46 to cushion any contact the laryngoscope blade 44 may have with a patient's teeth. Preferably, the padding layer 52 may be formed of gauze, sponge, or any other absorbent materials. Those of ordinary skill in the art will appreciate from this disclosure that any permeable or semi-permeable material may be used without departing from the scope of the present invention. Those of ordinary skill in the art will appreciate from this disclosure that the padding layer 52 may be formed of non-permeable and non-absorbent material without departing from the scope of the present invention. In some embodiments, the padding layer 52 may cover only a portion of the upper surface 60 of the container 54 rather than the entire upper surface 60. In other embodiments, the padding layer 52 may cover some or all of the connecting piece 68. The padding layer 52 may be affixed to the connecting piece 68 or may bend to cover the connecting piece 68 when the laryngoscope 40 is in use. In still other embodiments, the padding layer 52 cover the entire connecting piece 68 and may be affixed to the lower surface 62 of the container 54, covering a portion of the lower surface 62 not covered by the adhesive layer 56.

Referring to FIGS. 5-13 and 20-22, the adhesive layer 56 may be located on the lower surface 62 of the container 54 and is configured such that the accessory 50 may be temporarily affixed to the first major blade surface 46A of a laryngoscope blade 44, covering at least a portion of the first major blade surface 46A. The accessory 50 is preferably configured such that it only contacts one of the first and second opposing major blade surfaces 46A and 46B and covers at least a portion thereof. In the preferred embodiment, the adhesive layer 56 may cover only the portion of the first major blade surface 46A that is covered by the container 54, and preferably covers the entirety of the lower surface 62 of the container 54. However, in other embodiments the adhesive layer 56 may cover less that the entirety of the lower surface 62 of the container 54 so long as a sufficient portion is covered so as to ensure the accessory 50 remains affixed to the laryngoscope 40. The adhesive layer 56 is preferably configured to adhere with greater strength to the accessory 50 than the laryngoscope blade 44 such that the adhesive layer 56 may ensures that the accessory 50 does not slide or become detached from the laryngoscope 44 during use. However, the adhesive layer 56 preferably also allows the accessory 50 to be removed from the laryngoscope blade 44. Preferably, the accessory 50 may be removed without leaving adhesive behind, as this may make sterilization of the laryngoscope 40 more difficult.

The adhesive layer 56 is preferably formed of an adhesive which may be durable, water-proof, and non-toxic adhesive, such as acrylate adhesives and other medical adhesives. Those of ordinary skill in the art will appreciate from this disclosure that the adhesive layer 56 may be formed other adhesives and adhesive means without departing from the scope of the present invention. In some embodiments, the adhesive layer 56 may cover a portion of the lower surface 62 of the container 54 and a portion of the padding layer 52 in those embodiments wherein the padding layer 52 covers at least a portion of the connecting piece 68. In alternate embodiments, the adhesive layer 56 may be formed of Velcro or, alternatively, may be formed of one or more loops which may cover a portion of the second major blade surface 46B to secure the accessory 50 to the laryngoscope blade 44. In other embodiments, the adhesive layer 56 may be formed of magnets embedded in or affixed to the lower surface 62 of the container 54, allowing the accessory 50 to be detachably affixed to a laryngoscope blade 44 when a laryngoscope blade 44 is formed of materials which may attract magnets.

Referring to FIGS. 5-18, the accessory 30 may include a container 54 that may be preferably configured such that the padding layer 54 may be affixed to the upper surface 60 of the container 54 and the adhesive layer 56 may be affixed to the lower surface 62 of the container 54.

In the preferred embodiment, the container 54 may also include a connecting piece 68 which extends between the upper surface 60 and lower surface 62 of the container 54 connecting the two and defining a chamber 58 therein. In some embodiments, the container 54 may be configured to include a plurality of sides configured to extend generally non-planar parallel to the adhesive layer 56 when in use. These sides may form a connecting piece 68 connecting the upper surface 60 and lower surface 62. In some embodiments, the connecting piece 68 may form a flat side resembling a sidewall. In other embodiments, the connecting piece 68 may include a seam therein. In such an embodiment, the connecting piece 68 may resemble a seam, but may remain generally non-planar parallel to the adhesive layer 56, as the seam may form only a portion of the connecting piece 68.

In some embodiments, the container 54 may be flexible. In other words, the container 54 may be fully or partially comprised of flexible materials, such as soft plastic or rubber. Some or all of the upper surface 60, lower surface 62, and connecting piece 68 may be formed of a rigid or semi-rigid material, such as molded plastic, rubber or any other suitable material. It is preferred that the material used may be suitably strong so as to ensure that a vacuum may be applied to the container 54 will not collapse the chamber 58. In some embodiments, for example, the upper surface 60 of the container 54 may be flexible and the connecting piece 68 may be generally rigid. In such an embodiment, the upper surface 60 would flex inward, particularly about its axial center, with the connecting piece 68 retaining its shape. In an alternate embodiment, the upper surface 60 of the container 54 may be rigid such that the entire upper surface 60 may move relative to the lower surface 62 depending on the positioning of the connecting piece 68 which is flexible. In such an embodiment, pressure forcing the upper surface 60 inward would cause the entire upper surface to lower while retaining its shape, while the connecting piece 68 flexes outward. However, those of ordinary skill in the art will appreciate from this disclosure that materials which would collapse if a vacuum is applied may be used without departing from the scope of the present inventions, as support partitions 70 may be placed within the chamber 58 to provide greater stability. In still other embodiments, the container 54 may be comprised of several layers of soft plastic which may be inflated to insure a measure of rigidity when placed under vacuum. Those of ordinary skill in the art will appreciate from this disclosure that the container 54 may be formed of any suitable material without departing from the scope of the present invention.

The container 54 is preferably further configured such that it may define a chamber 58 and at least one channel 64 in the outer surface 65 of the container 54. The channel may be configured to allow liquid to reach the inner surface 66 of the container 54. In the preferred embodiment, a plurality of channels 64 may be present in the outer surface 65 of the container 54. These channels 64 may be of any size, and may be included in varying or non-uniform sizes. It is preferred that the number of channels 64 are provided in the range of 10 to 80 channels. More preferably, the number of channels 64 may be in the range of 25-75 channels 64. Those of ordinary skill in the art will appreciate from this disclosure that any number of channels 64 may be provide to ensure liquid can adequately reach an inner surface 66 of the container 54 without departing from the scope of the present invention.

Referring to FIGS. 5-8 and 11-13, in one preferred embodiment, the at least one channel 64 may be present in the outer surface 65 of the container 54. In some embodiments, the at least one channel 64 may be present in the upper surface 60 of the container 54 and the padding layer 54 may cover at least one channel 65. In such a configuration, liquid may pass into the padding layer 54 and then may move through at least one channel 64 to enter into the chamber 58. Once inside the chamber 58, the liquid may contact the inner surface 66 of the container 54. This path is depicted by the arrows in FIGS. 5-8. In other embodiments, some of the least one channels 64 may extend through the plurality of sides of the container 54 forming the connecting piece 68 such that some liquid may enter the container 54 without passing through the padding layer 52. In still other embodiments, some of the at least one channels 64 may extend through the plurality of sides of the container 54 forming the connecting piece 68 and the padding layer 52 may also extend over the plurality of sides forming the connecting piece 68. This may allow liquid entering the chamber 58 via the channels 64 in the plurality of sides forming the connecting piece 68 to pass through the padding layer 52 prior to entering the chamber 58 even when traversing the connecting piece 68. The padding layer 52 may be affixed to the connecting pieces 68 and upper surface 60, or to the upper surface 60 alone exposing the channels 64 to patients directly. In still other embodiments, at least one channel 64 may also be present in the lower surface 62 of the container 54, wherein the channels 64 are only present in the portion of the lower surface 62 not covered by the adhesive layer 56. In such an embodiment, the padding layer 52 may fully cover the connecting piece 68 and may also cover a portion of the lower surface 62 of the container 54.

Referring to FIGS. 1-2 and 9-14, the accessory 50 may include a tube 82 which may define a passageway 84 therethrough. The tube 82 may be connected to the container 54 and may place the passageway 84 in fluid connection with the chamber 58, which may allow liquid and/or air to travel from the container 54 through the passageway 84 in the tube 82. The accessory 50 may also include a suction device 86 which may be attached to the tube 82 to draw air and liquid from the chamber 58 through the tube 82 to create a vacuum in the chamber 58. The tube 82 is preferably configured to transfer a vacuum to the chamber 58 such that liquid that enters the container 54 may be removed from the chamber 58 via the passageway 84 regardless of whether the liquid travels through the padding layer 52 first. This allows the suction device 86 which may be connected to the tube 82 to pull liquid and/or air from the chamber 58 within the container 54 out through the passageway 84 in the tube 82. The suction device may be formed of standard wall suction provided in most hospitals, a portable vacuum device, or any other suitable means for imparting suction onto the passageway 84 in the tube 82. In some embodiments, the tube 82 may be connected to a suction device 86 to draw air and liquid through the accessory 50. The arrows in FIGS. 9-10 and 13-14 depict the path liquid and/or air may follow when vacuum is applied to the chamber 58. The tube 82 may also provide additional safety for the device, ensuring that the accessory 50 will not be lost in a patient's mouth or throat should the accessory 50 come loose from the laryngoscope blade 44 during use. In some cases, the tube 82 may remain affixed to the accessory 50 so that the accessory 50 may be pulled from a patient's throat by pulling on the tube 82, guiding the accessory 50 out from the patient's throat.

Referring to FIGS. 9-17, in the preferred embodiment the container 54 may further include first and second axial ends 74 and 76 respectively. The first axial end 74 may preferably be nearer to the laryngoscope handle 32 and the second axial end 76 may preferably be nearer to the blade tip 42. The container may further comprise first and second lateral ends 78 and 80 running the length of the laryngoscope blade 44 and being perpendicular to the first axial end 74 and second axial ends 76. In the preferred embodiment, the container 54 preferably further comprises a port 72, which may be included where the first axial end 54 meets the first lateral end 78. Alternatively, in some preferred embodiments the port 72 may be included where the first axial end 54 meets the second lateral end 80, or may be included at any other place on the container 54. The port 72 is preferably configured to detachably receive the tube 82 in manner which allows air and liquid to be sucked through the passageway 84 in the tube 82 without escaping through gaps in the port 72. However, those of ordinary skill in the art will appreciate from this disclosure that the tube 82 may be affixed directly to any portion of the container 54 without departing from the scope of the present invention. It is preferred that the tube 82 be configured to be attached to standard wall suction tubing which is commonly present in hospitals. Those of ordinary skill in the art will appreciate from this disclosure that the tube 82 may be configured to be affixed to any suction device without departing from the scope of the present invention.

Referring to FIGS. 11-18, the container 54 may include a plurality of support partitions 70 located in the chamber 58 and configured to guide fluid therein. In the preferred embodiment, the support partitions 70 may extend upward from the lower surface 62 of the container 54 without reaching the upper surface 60. This may form a gap 71 between the upper surface 60 and the support partitions 70. The gap 71 may allow the upper surface 60 of the container 54 to flex inward if necessary, with the support partitions 70 providing possible support to ensure the container 60 cannot flex so far as to collapse the chamber 58.

The support partitions 70 may be formed in any shape which may provide additional support to the container 54, including cylindrical, conical, rectangular, or other shapes. In some embodiments, the plurality of support partitions 70 may be located in an inner surface 66 of the container 66 and may have a generally conical shape. In other embodiments, the plurality of support partitions 70 may be located in an inner surface 66 of the container 66 and may have be rectangular in cross section. The shape of the support partitions 70 may affect the flow of liquid and/or air throughout the container. When the support partitions 70 are conical or cylindrical, liquid and/or air may enter follow a path around either side of each support partition 70 and out through the passageway 84 in the tube 82, as depicted by the arrows in FIG. 18. Depending on the number of support partitions 70 and channels 64, liquid and/or air may follow numerous variable paths as it travels within the chamber 58. As depicted by the arrows in FIG. 14, rectangular support partitions 70 which may run a significant portion of the length of the chamber 58, may cause liquid and/or air in the chamber 58 to follow a path between either two support partitions 70 or one of the support partitions 70 and either first or second lateral ends 78 and 80, and out through the passageway 84 in the tube 82. Depending on the number of support partitions 70, liquid may follow a proportional number of paths as it travels within the chamber 58. For example, in the embodiment depicted in FIGS. 7-10, the accessory 50 may comprise five support partitions 70 defining six paths for liquid to travel along as it travels from one side of the chamber 58 to the tube 82. Preferred embodiments of the accessory 50 may include any number of support partitions 70 provided that the support partitions 70 can provide adequate support to the container 54 while still allowing room in the chamber 58 for liquid. Preferably, this means that the support partitions 70 may account for less than 40 percent of the volume of the container 54. More preferably, the support partitions 70 may account for less than 33 percent of the volume of the container 54. Those of ordinary skill in the art will appreciate from this disclosure that the support partitions 70 may be provided in any number, shape, or combination of shapes without departing from the scope of the present invention.

The support partitions 70 may further allow the user of the laryngoscope 30 and accessory 50 to control the suction within the chamber 58. By applying greater pressure onto the laryngoscope blade 44, the user may press the accessory 50 against the patient's tongue, causing the container 54 to flex inwards until the gap 71 is filled. This may partially collapse the chamber 58 and cause the suction to be amplified. If the user requires less suction, less pressure may be applied to the laryngoscope blade 44 and the chamber 58 may maintain its full shape. With greater volume for the suction to be applied to, the vacuum imparted on the chamber 58 may be lessened. In some embodiments, the support partitions 70 may be fully flexible, to allow the user to fully collapse the chamber 54 and cease suction in the chamber 54.

Figure 13:
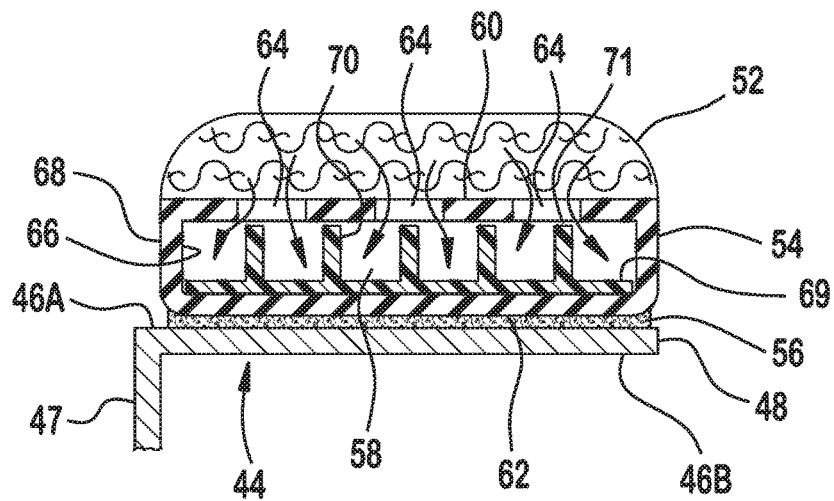
Figure 14:
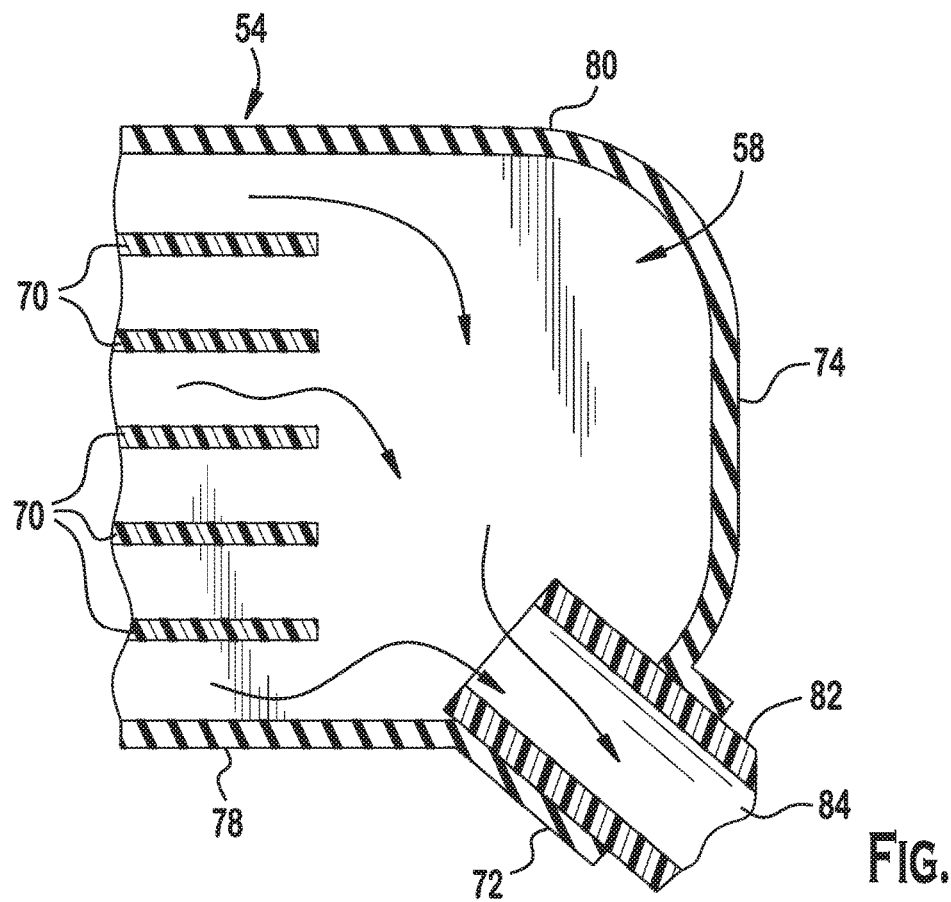
FIG. 14 is a partial schematic view of a portion of the accessory of FIG. 11 demonstrating that the support partitions 70 may be roughly rectangular, and may create varying paths for allow liquid and/or air to travel through, as depicted by arrows.
Figure 15:
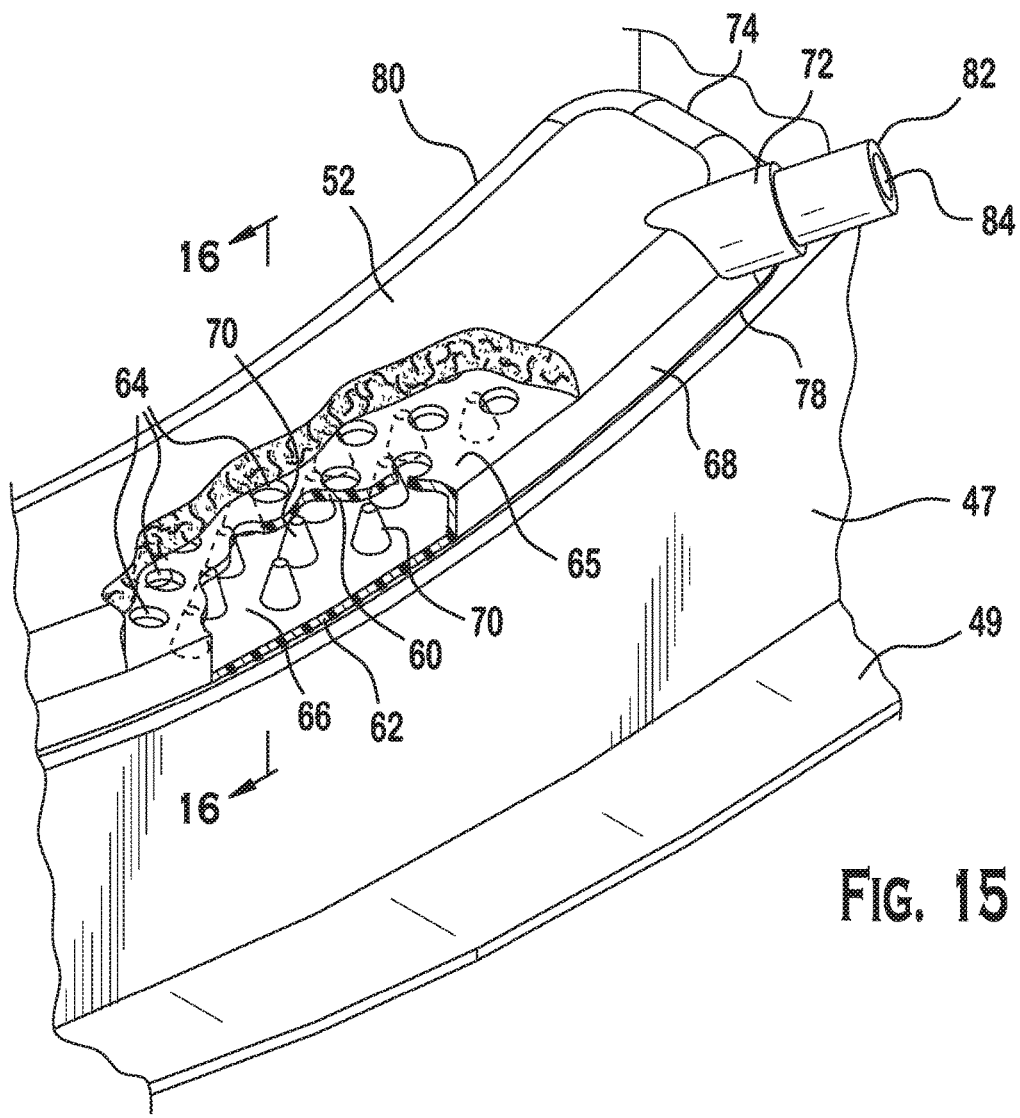
Figure 16:
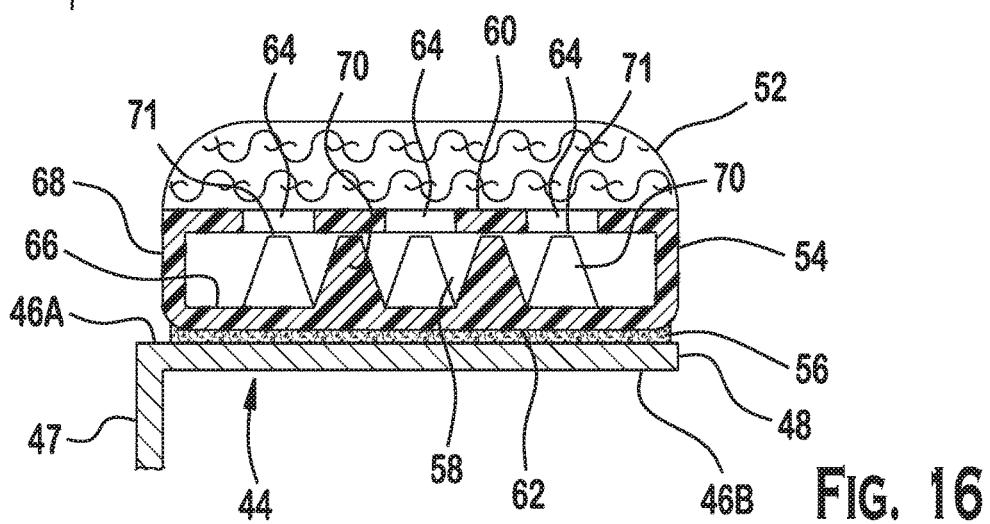
FIG. 16 is a cross-sectional view of a portion of the laryngoscope and accessory of FIG. 15 as taken along the lines 16-16 of FIG. 15 demonstrating that a gap 71 may be included between each support partition 70 and the upper surface 60 of the container 54 when the support partitions are roughly conical in shape. This may allow the container to flex while adding greater stability to the container 54, ensuring the chamber 58 is properly defined.
Figure 17:
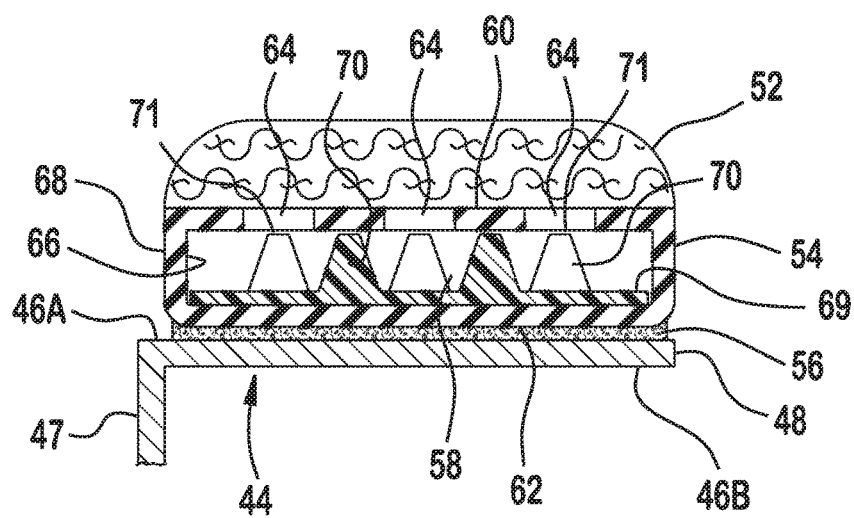
Figure 18:
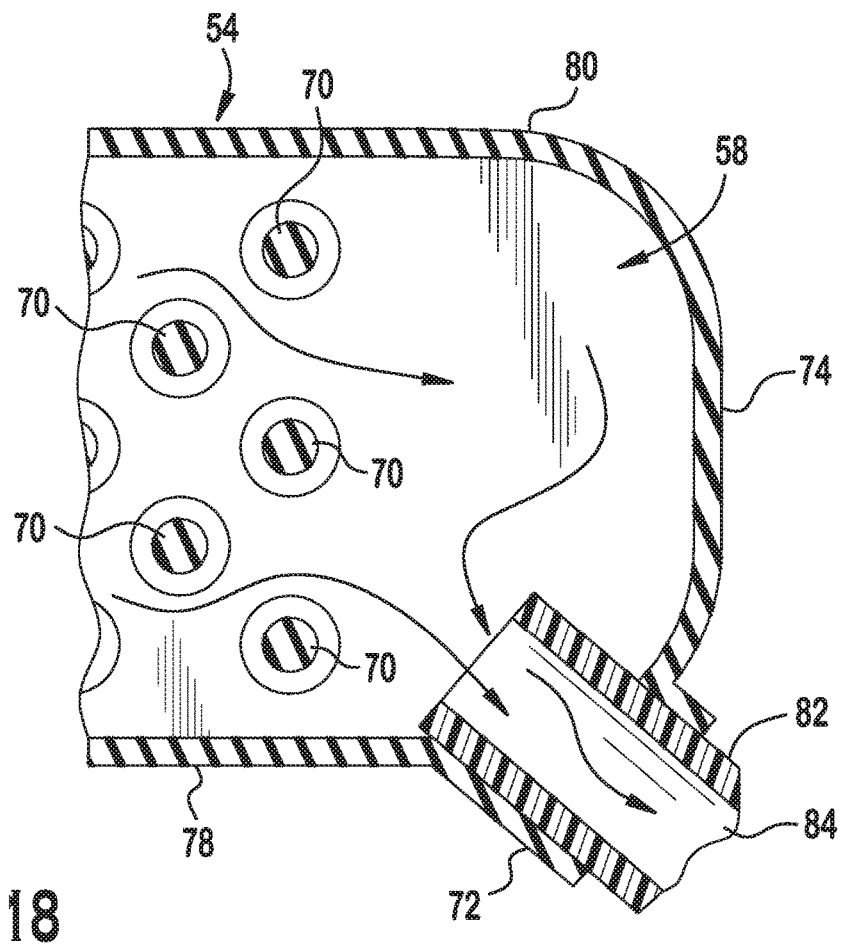
FIG. 18 is a partial schematic view of a portion of the accessory of FIG. 15 demonstrating that the support partitions 70 may be roughly conical in shape and not connected to the other support partitions 70. This may create numerous varying paths for liquid and/or air to travel through, as depicted by arrows.
Figure 19:
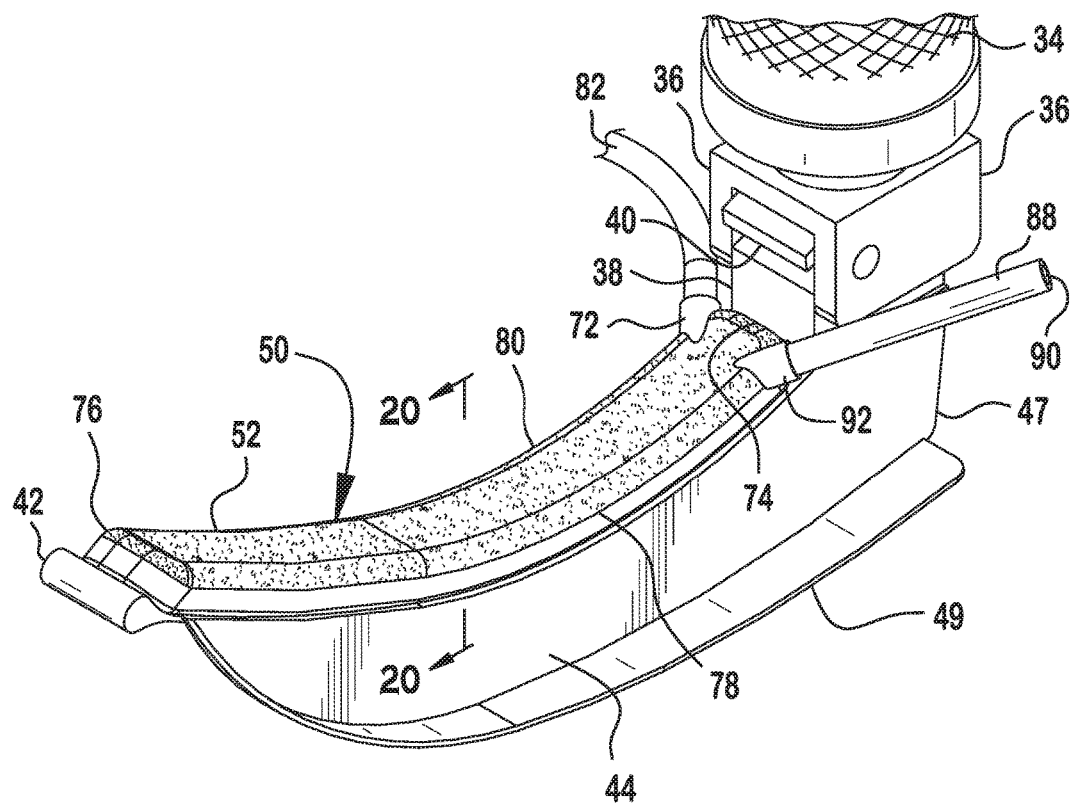
FIG. 19 is a partial perspective view of an alternate preferred embodiment of the accessory demonstrating that the accessory 50 may further comprise a second tube 88 defining a second passageway 90 inserted into a second port 92. In this embodiment, the first tube 82 may be inserted into the first port 72 which may be located between the first axial end 74 and second lateral end 80 of the container 54, and the second tube 88 may be inserted into a second port 92 located between the first axial end 74 and first lateral end 78 of the container 54. However, in other embodiments, the first tube 82 and/or first port 72 may be located on the second axial end 76, and may be located between the second axial end 76 and first lateral end 78. In such an embodiment, both the first tube 82 and second tube 88 may located along the first lateral end 78.
Figure 20:
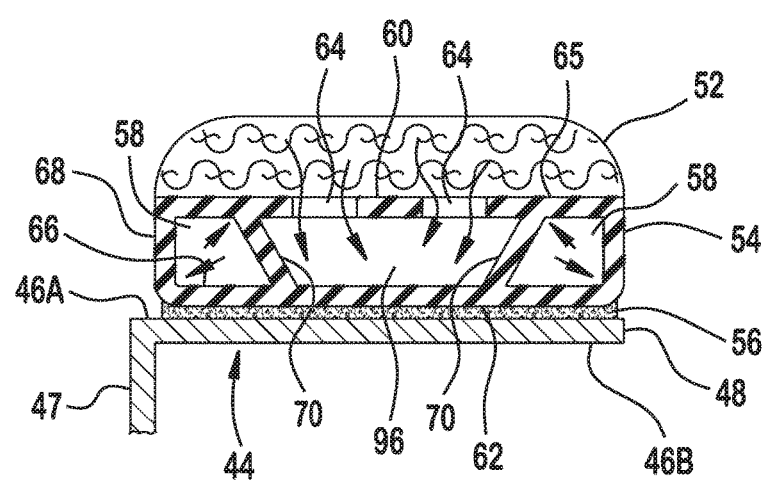
FIG. 20 is a cross-sectional view of a portion of the laryngoscope and accessory of FIG. 19 as taken along the lines 20-20 of FIG. 19 demonstrating that in some embodiments, the support partitions 70 may define a sub-container 96 within the container 54. Preferably, the channels 64 may be positioned only above the sub-container 96 such that liquid and/or air may enters the sub-container rather than the rest of the chamber 58.
Figure 21:
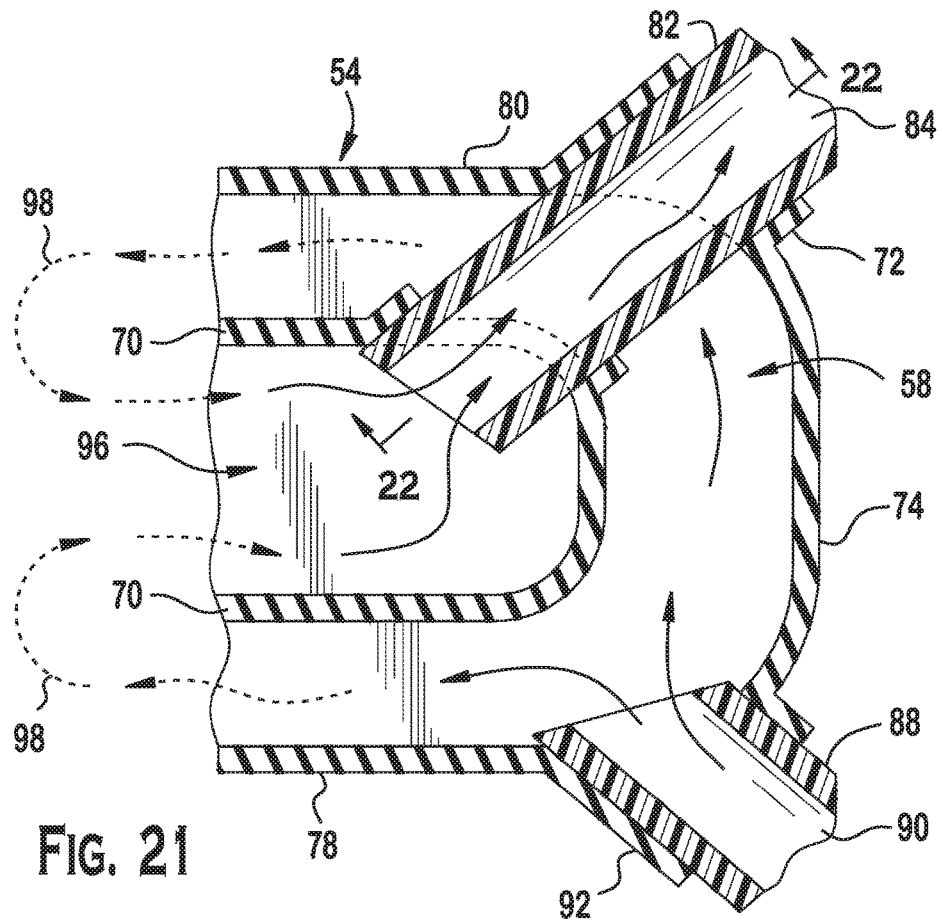
FIG. 21 is a partial schematic view of an alternate portion of the accessory of FIG. 19 demonstrating that the second tube 88 should preferably be affixed to a reverse suction device 94 and connected directly to the container 54, and the first tube 82 being affixed to a suction device 86 and connected directly the sub-container 96. The lines demonstrate that air may be pushed through the second passageway 90, into the chamber 58, then into the sub-container, and out through the first passageway 84 in the first tube 82. A pressurized flow path 98 is show with dashed arrows to better illustrate vacuum within the chamber 58 and/or sub-container 96.

Referring to FIGS. 13 and 17, in some embodiments the support partitions 70 may be formed of a single piece with multiple upward protrusions connected a single insert flange 69. In such an embodiment, the insert flange 69 may be located within the chamber 54 and the plurality of support partitions 70 may be located thereon. The support partitions 70 and insert flange 69 may be formed of a separate piece than the container 54. The insert flange 69 may be affixed to the inner surface 66 of the container 54 covering a portion of the inner surface 66 and filling a portion of the chamber 58 along with the support partitions 70. Alternatively, the insert flange 69 and support partitions 70 may be placed within the chamber 58 but not affixed to the inner surface 66 to allow these pieces to move about the chamber 58. In such embodiments, the support partitions 70 may be made of a different material than the container 54, which may be preferable to provide additional stability to the chamber 58. For example, if the container 54 is formed of rubber and the support partitions 70 are formed of molded plastic, the container 54 may be able to flex downward or outward, filling the gap 71 until the upper surface 60 abuts the support partitions 70. This may allow flexibility of the container 54 to be provided for and controlled in certain embodiments. In other embodiments, springs may be provided to provide additional support to the container 54 while maintaining flexibility. Those of ordinary skill in the art will appreciate from this disclosure than any suitable material may be used for the container 54 and the support partitions 70 without departing from the scope of the present invention.

Referring to FIGS. 19-24, the accessory 50 may include a second tube 88 connected to the container 54 and in fluid connection with the chamber 58 in the container 54. The second tube 88 may transfer a positive pressure to the chamber 58 to prevent the chamber 58 from closing due to the flexibility of the container 54 and the vacuum created therein. The second tube 88 may define a second passageway 90 that is also connected to the chamber 58. The second tube 88 may be connected to a reverse-suction device 94 to impart a positive pressure. In such an embodiment, air may be pushed from the reverse-suction device 94 into the chamber 58 through the second passageway 90 in the second tube 88. This can facilitate the creation of a vacuum within the container 54. Those of ordinary skill in the art will appreciate from this disclosure that additional tubes and suction devices may be added without departing from the scope of the present invention.

In some embodiments, the first tube 82 may be inserted into a second port 92 located where the first axial end 74 meets the second lateral end 80 and the second tube 88 may be inserted into a first port 82 where the first axial end 74 meets the first lateral end 78. Those of ordinary skill in the art will appreciate from this disclosure that the first port 82 and/or second port 92 may be located on any portion of the container 54 without departing from the scope of the present invention. Those of ordinary skill in the art will also appreciate from this disclosure that the first tube 82 and/or the second tube 88 may be affixed directly to any portion of the container 54 without departing from the scope of the present invention. In other preferred embodiments, the first tube 82 and/or first port 72 may be located on the second axial end 76, and may be located between the second axial end 76 and first lateral end 78. In such an embodiment, both the first tube 82 and second tube 88 may located along the first lateral end 78. Those of ordinary skill in the art will also appreciate from this disclosure that the first tube 82 and/or the second tube 88 may be affixed directly to any portion of the container 54, including either axial end, without departing from the scope of the present invention.

Figure 22:
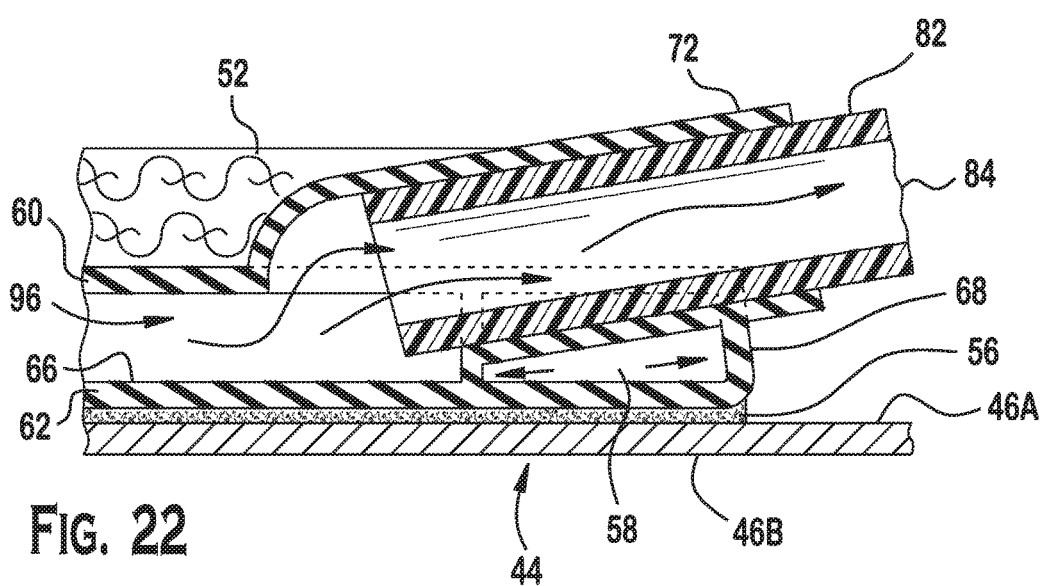
FIG. 22 is a cross-sectional schematic view of the portion of the accessory of FIG. 21 as taken along the lines 22-22 of FIG. 21, demonstrating that in some embodiments, the first port 72 and first tube 82 may connected to the sub-container 96, and space may be provided under the first port 72 such that the first port 72 does not fully divide the chamber 58.
Figure 23:
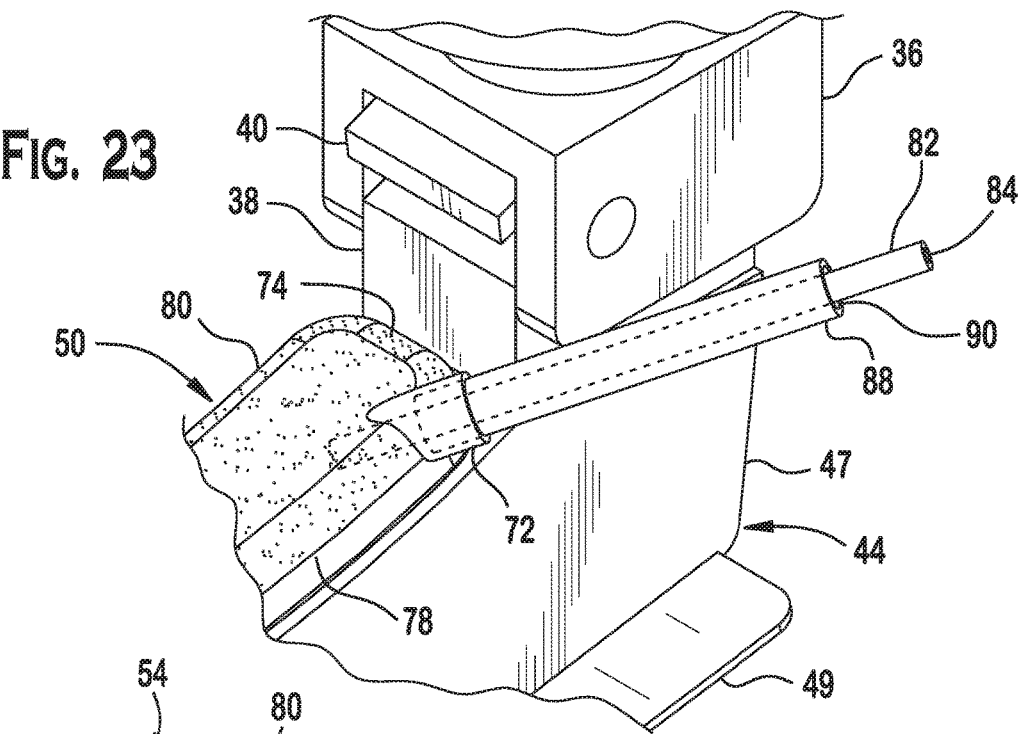
FIG. 23 is a partial perspective view of an alternate preferred embodiment of the accessory 50 wherein the accessory 50 may include a second tube 88 defining a second passageway 90, and wherein the first tube 82 may be inserted into the second passageway 90, with both being inserted into the first port 72.
Figure 24:
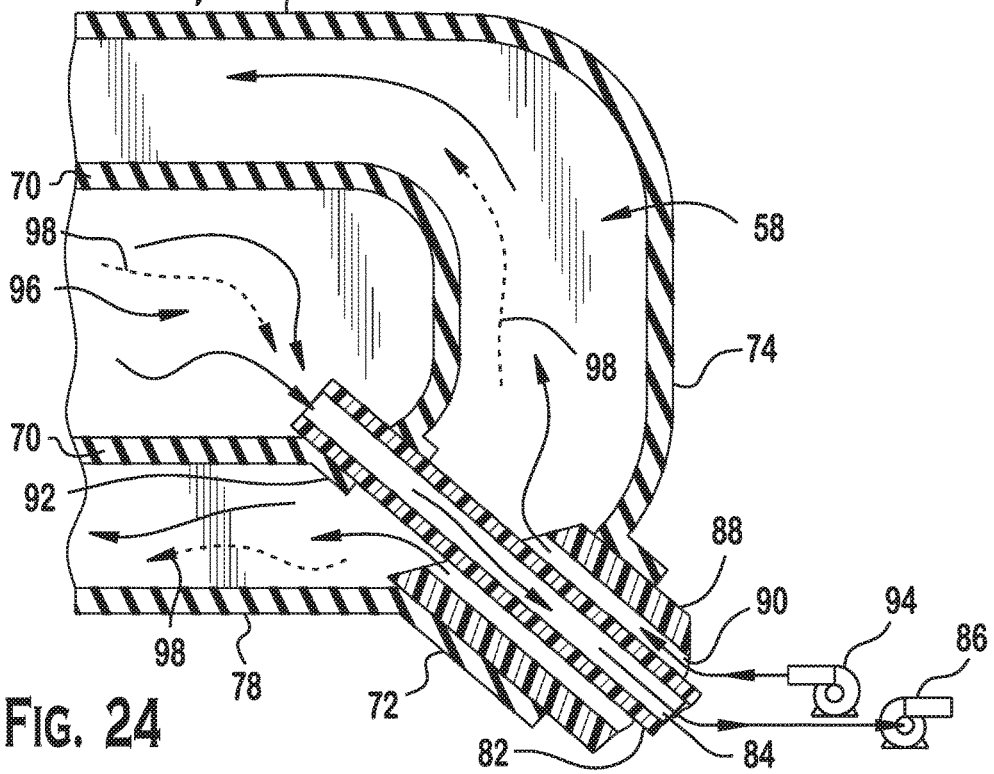
FIG. 24 is a partial schematic view of a portion of the accessory of FIG. 23 demonstrating that in some embodiments the first tube 82 may attached to suction device 82 and inserted into the second port 92 built into the sub-container 96. The second tube 88 may be attached to a reverse-suction device 94 and connected to the chamber 58. The arrows indicate that path that air and/or liquid may follow when passing through the accessory 50. Air may be pushed through the second passageway 90, into the chamber 58, then into the sub-container 96, and out through the first passageway 84 in the first tube 82. A pressurized flow path 98 is show with dashed arrows to better illustrate vacuum within the chamber 58 and/or sub-container 96.

In some embodiments, the support partitions 70 may form one or more roughly rectangular or ovular sub-containers 96 which may be open to the second passageway 90 on one end and to the chamber 58 via an opening in proximity to the second axial end 76. In such a configuration, the second tube 82 may push air into the chamber 58 at the first axial end 74 such that the air may be forced around both edges of the chamber 58. The air may then enter the sub-container 96 through an opening in the support partitions, potentially increasing the vacuum which may be applied to the sub-container 96 by the suction device 86 attached to the first tube 82. Some potential paths for this air are depicted by the arrows in FIGS. 21 and 22. It is preferred that the port 72 in such embodiments, as seen in FIG. 22, may protrude through the chamber 58 in such a way that it allows air to move under or around it within the chamber 58, rather than fully dividing the chamber 58. This may facilitate the movement of air with the chamber 58 and increase the potential suction created by the reverse-suction devices 94 and suction device 86 working in unison. It is preferred that the channels 64 in this embodiment may be present in the upper surface 60 of the container 54 only above the sub-container 96, as this is the area in which the greatest suction would be applied. In other configurations, a sub-container 96 need not be defined by support partitions 70. Those of ordinary skill in the art will appreciate from this disclosure that any means for imparting vacuum on the chamber 58 may be used without departing from the scope of the present invention.

In some embodiments, the sub-container 96 may be fully closed off from the chamber 58, allowing the second tube 88 attached to a reverse-suction device 94 to inflate the chamber to maintain the shape of the container 54. In some embodiments, the reverse-suction device may be a syringe, a blower, or any other suitable means for pushing air into the accessory 50. In some embodiments embodiment, the container 54 may include more than one sub-container 96 located within the chamber 58 and at least one of the sub-containers 96 does not have any of the at least one channels connecting thereto. In such embodiments, only the sub-containers 96 connected to the at least one channels 64 may be imparted with a vacuum. The sub-containers 96 not connected to the at least one channels 64 may be imparted with reverse-suction to inflate a portion of the container 54 to increase stability. In these embodiments, the first tube 82 may be attached to a suction device 86 and configured to draw air and/or liquid through the outer surface 65 of the container 54 into the sub-container 96, and out through the passageway 84 in the first tube 82 without affecting the shape of the container 54.

In some embodiments, the first tube 82 and second tube 88 may be positioned such that one is located within the other. In some embodiments, the second tube 88 may be positioned concentrically within the first tube 82. In other embodiments, the first tube 82 may be positioned concentrically within the second tube 88. As an example of how these configurations may function, FIGS. 23 and 24 demonstrate one preferred embodiment in which the second tube 88 may define a second passageway 90 into which the first tube 82 may inserted, with both being inserted into the first port 72. The first tube 82 may be attached to suction device 82 and may be inserted into the second port 92 built into the sub-container 96. The second tube 88 may be attached to a reverse-suction device 94 and may be connected to the chamber 58. The arrows indicate paths that fluid, such air and/or liquid, may follow when passing through the accessory 50, traveling through the second passageway 90, into the chamber 58, then into the sub-container 96, and out through the first passageway 84 in the first tube 82. The dashed arrows indicate a pressurized flow path 98. The plurality of support partitions 70 define at least one pressurized flow path 98 which extends between the first tube 82 and second tube 88. The pressurized flow path 98 may be formed through the reverse-suction and suction which may be imparted onto the accessory 50 by the suction device 86 and reverse-suction device 94 when both are connected to the accessory 50. At least one channel 64 is preferably cut out of the upper surface 60 above the sub-container 96. This allows liquid and/or air to enter the sub-container 96 and out through the first tube 82 into the suction device 86. In another preferred embodiment, the sub-container 96 may be fully closed off from the chamber 58, allowing the second tube 88 attached to a reverse-suction device 94 to inflate the chamber to maintain the shape of the container 54. The first tube 82 in such an embodiment may be attached to a suction device 86 and configured to draw air and/or liquid through the outer surface 65 of the container 54 into the sub-container 96, and out through the passageway 84 in the first tube 82 without affecting the shape of the container 54.

In one embodiment, the present invention may operate as follows. A laryngoscope 30 may be provided preferably having a handle 32 and blade 44, the blade preferably having a first major blade surface 46A on the inner curve of its blade 44 and a second major blade surface 46B on the outer curve of the blade 44. An accessory 50 may be provided preferably having an adhesive layer, a container 54 defining at least one chamber 58, a padding layer 52, and a tube 82 connected to the chamber 58. Preferably, the accessory 50 may be affixed to the first major blade surface 46A of the laryngoscope 30. A suction device 86 may then be connected to the tube 82 and activate, creating a vacuum with in the chamber 58. This may cause the container 54 to bend at the connecting piece 68 as the upper surface 60 is pulled downward. Alternatively, this may cause the upper surface 60 to bend inward, and it may fill the gap 71 and come to rest on the support flanges 70. The laryngoscope 30 with accessory attached 50 may then be used on a patient, with the accessory 50 being placed directly on the patient's tongue. As upward pressure is applied to the handle 32, this pressure is transferred to the laryngoscope blade 44, causing the patient's tongue and jaw to be pushed upward and outward to expose the trachea. An intubation tube may be pushed along the guide flange 47 and abutment plate 49 as it is guided into the trachea. During this process, fluid such as saliva or blood may enter the chamber 58 through the channels 64, with or without passing through the padding layer 52. Once in the chamber 58, the fluid may then follow one or more path as it contacts an inner surface 66 of the container, eventually traveling up the passageway 84 in the tube 82 and into the suction device 86. If excess pressure is applied to the laryngoscope 30, the padding layer 52 may come in contact with the teeth of the patient, preventing direct contact between the teeth and the laryngoscope blade 44. Once the patient has been intubated, pressure on the laryngoscope handle 32 may be relaxed and the laryngoscope 30 may be removed from contact with the patient. The tube 82 may then be disconnected from the suction device 86. The adhesive layer 56 may then be released from the first major blade surface 46A, causing the accessory 50 to be released from the laryngoscope 30. The accessory 50 may then be discarded, and the laryngoscope 30 may be sterilized. Once sterilized, the laryngoscope 30 may then be provided again for use with a new accessory 50, allowing this process to begin anew.

Figure 25:
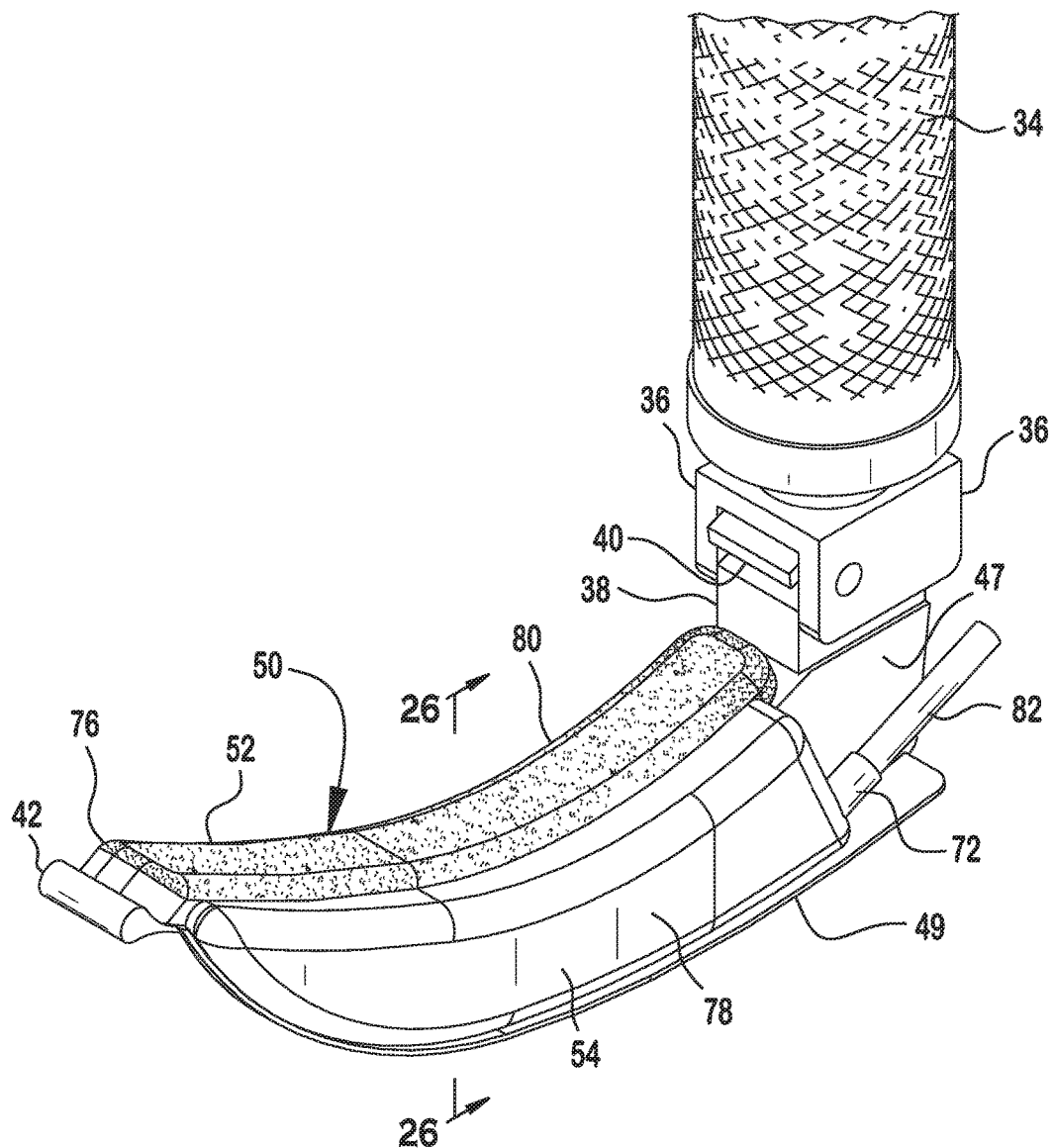
FIG. 25 is a front perspective view of a laryngoscope 30 with the accessory 50 attached, wherein the padding layer 52 may be present along the first major blade surface 46A of the laryngoscope blade 44 and wherein the container 54 may be present on the guide flange 47 by roughly perpendicular to the padding layer 52. The tube 82 may be present on the left side of the user, depending on how the laryngoscope 30 is held, to increase visibility of the throat during intubation.
Figure 26:
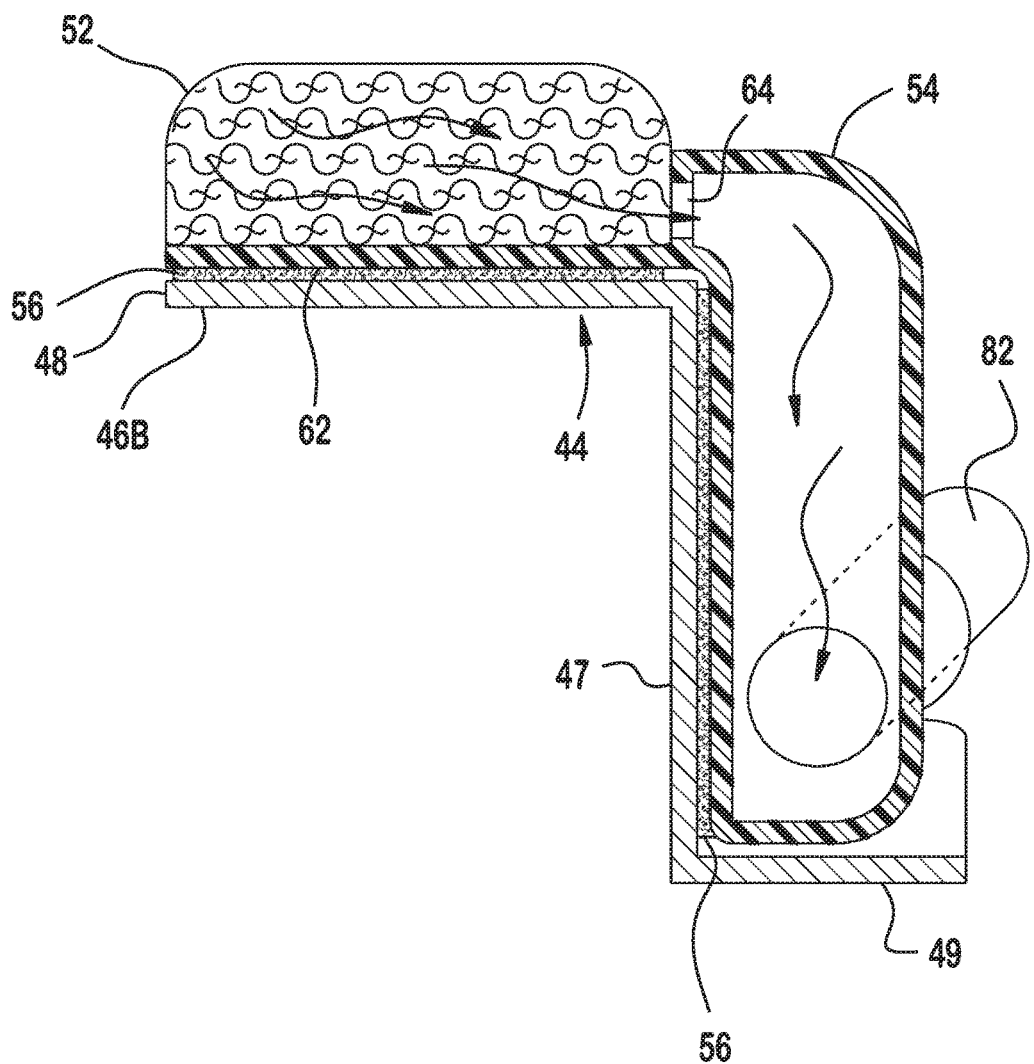
FIG. 26 is a cross-sectional view of a portion of the laryngoscope and accessory of FIG. 25 as taken along the lines 26-26 of FIG. 25 wherein the padding layer 52 may be affixed to a portion of the lower surface 62 of the container 54 which may extends along the first major blade surface 46A of the laryngoscope blade 44 and may be affixed thereto by the adhesive layer 56. In such an embodiment, the container 54 may not be present on the first major blade surface 46A but instead may be affixed to the guide flange 47 by the adhesive layer 56.

Referring to FIGS. 25 and 26, in some embodiments the chamber 58 may not be present between the padding layer 52 and adhesive layer 56. In one preferred embodiment, a portion of the lower surface 62 of the container 54 may be present between the padding layer 52 and adhesive layer 56 and affixed to the first major blade surface 46A. The upper surface 60 of the container 54 and connecting piece 68 may be formed roughly perpendicular to the first major blade surface 46A, defining the chamber 58 roughly perpendicular to the padding layer 52. In some embodiments, the lower surface 62 of the container 54 may be bent to follow the outline of the laryngoscope blade 44 and guide flange 47, being bent roughly 90 degrees. In such embodiments, the adhesive layer 56 may be present along the first major blade surface 46A and guide flange 47 below the lower surface 62, affixing the accessory 50 to both surfaces. In such embodiments, the tube 82 may be placed along the guide flange 47 to be better kept from impeding the user's view of the patient's throat. It is preferred that the tube 82 be affixed to a portion of the container which will keep the tube 82 on the user's left hand side. However, those of ordinary skill in the art will appreciate from this disclosure that the tube 82 may be affixed directly to any portion of the container 54 without departing from the scope of the present invention.

Figure 27:
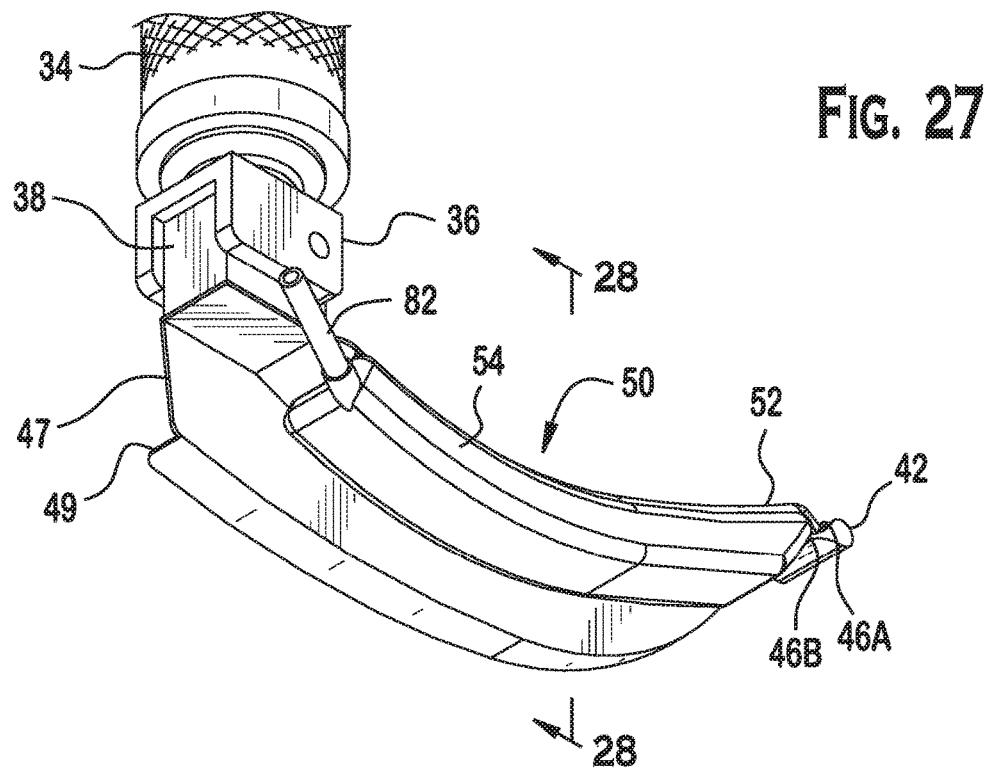
FIG. 27 is a partial rear perspective view of a laryngoscope blade 44 with the accessory 50 attached, wherein the padding layer 52 may be present along the first major blade surface 46A of the laryngoscope blade 44 and wherein the container 54 may be present on the second major blade surface 46B and may by roughly parallel to the padding layer 52. The tube 82 may be present behind the guide flange 47 and may be on the left side of the user depending on how the laryngoscope 30 is held, to increase visibility of the throat during intubation.
Figure 28:
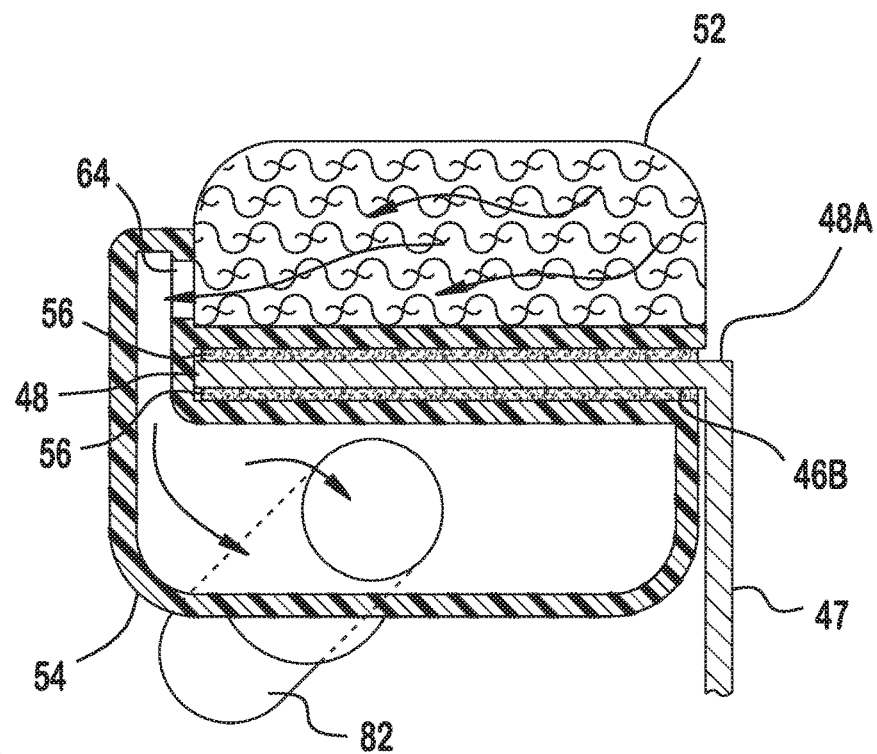
FIG. 28 is a cross-sectional view of a portion of the laryngoscope and accessory of FIG. 27 as taken along the lines 28-28 of FIG. 27 wherein the padding layer 52 may be affixed to a portion of the lower surface 62 of the container 54 which may extends along the first major blade surface 46A of the laryngoscope blade 44 and may be affixed thereto by the adhesive layer 56. The chamber 58 may extend upward above the laryngoscope blade 44 and the at least one channel 64 may be present to allow fluid to travel from the padding layer 52 and into the chamber 58. In such an embodiment, the container 54 may affixed to the second major blade surface 46B and may by roughly parallel to the padding layer 52. The tube 82 may be present behind the guide flange 47 and may be on the left side of the user depending on how the laryngoscope 30 is held, to increase visibility of the throat during intubation.

Referring to FIGS. 27 and 28, a portion of the lower surface 62 of the container 54 may be present between the padding layer 52 and adhesive layer 56 and affixed to the first major blade surface 46A. The chamber 58 may be defined below the laryngoscope blade 44 roughly parallel to the padding layer 52. In such an embodiments, the lower surface 62 of the container 54 may be bent in a rough U-shape 90 degrees, covering both the first and second major blade surfaces 46 and the minor blade surface 48. In such embodiments, the adhesive layer 56 may be present along the first and second major blade surfaces 46 and the minor blade surface 48 as well, such that it is between these surface and the lower surface 62 of the container 54, affixing the accessory 50 to all of these surfaces. In such embodiments, the tube 82 may be placed below the laryngoscope blade 44 and behind the guide flange 47 to be better kept from impeding the user's view of the patient's throat. It is preferred that the tube 82 be affixed to a portion of the container which will keep the tube 82 on the user's left hand side. However, those of ordinary skill in the art will appreciate from this disclosure that the tube 82 may be affixed directly to any portion of the container 54 without departing from the scope of the present invention.

It is recognized by those skilled in the art that changes may be made to the above described accessory 50 without departing from the broad inventive concept thereof. It is understood, therefore, that this invention is not limited to the particular embodiments disclosed, but is intended cover all modifications which are within the spirit and scope of the invention as defined by the above specification, the appended claims and/or shown in the attached drawings.

What is claimed is:

1. An accessory configured for detachable placement on a blade of a laryngoscope, the blade having first and second opposing major blade surfaces, the accessory comprising:
   a container defining a chamber therein, the container having an upper surface and a lower surface, at least one channel is formed in an outer surface of the container such that liquid can enter the chamber;
   a tube defining a passageway therethrough and connected to the container, the passageway being in fluid communication with the chamber,
   a padding layer comprised of absorbent material and located on the upper surface of the container;
   an adhesive layer located on the lower surface of the container such that the accessory is configured to be temporarily affixed to the blade of the laryngoscope, the accessory being configured to only contact one of the first and second opposing major blade surfaces and to cover at least a portion thereof, the tube being configured to transfer a vacuum to the chamber such that liquid that enters the container, regardless of whether the liquid travels through the padding layer first, can be removed from the chamber via the passageway; and a plurality of support partitions located in the chamber and configured to guide fluid therein.

2. The accessory of claim 1, wherein the container has a plurality of sides configured to extend generally non planar parallel to the adhesive layer when in use and to form a connecting piece between the upper surface and the lower surface, some of the at least one channels extend through the plurality of sides of the container such that some liquid can enter the container without passing through the padding layer.

3. The accessory of claim 2, wherein the connecting piece includes a seam therein.

4. The accessory of claim 2, wherein the upper surface of the container is flexible and the connecting piece is generally rigid.

5. The accessory of claim 1, wherein the container has a plurality of sides configured to extend generally non planar parallel to the adhesive layer when in use and to form a connecting piece between the upper surface and the lower surface, wherein some of the at least one channels extend through the plurality of sides of the container, the padding layer also extending over the plurality of sides such that liquid entering the chamber via the some of the at least one channels in the plurality of sides passes through the padding layer prior to entering the chamber even when traversing the plurality of sides.

6. The accessory of claim 1, further comprising a suction device attached to the tube to draw air and liquid from the chamber through the tube to create the vacuum in the chamber.

7. The accessory of claim 1, wherein the plurality of support partitions are located on an inner surface of the container and are one of generally conically shaped and formed by springs.

8. The accessory of claim 1, wherein the plurality of support partitions are located on an inner surface of the container and are rectangular in cross section.

9. The accessory of claim 1, wherein an insert flange is located within the chamber with the plurality of support partitions being located thereon.

10. The accessory of claim 9, wherein the container is flexible.

11. An accessory configured for detachable placement on a blade of a laryngoscope, the blade having first and second opposing major blade surfaces, the accessory comprising:

a container defining a chamber therein, the container having an upper surface and a lower surface, at least one channel is formed in an outer surface of the container such that liquid can enter the chamber;

a tube defining a passageway therethrough and connected to the container, the passageway being in fluid communication with the chamber, a padding layer comprised of absorbent material and located on the upper surface of the container;

an adhesive layer located on the lower surface of the container such that the accessory is configured to be temporarily affixed to the blade of the laryngoscope, the accessory being configured to only contact one of the first and second opposing major blade surfaces and to cover at least a portion thereof, the tube being configured to transfer a vacuum to the chamber such that liquid that enters the container, regardless of whether the liquid travels through the padding layer first, can be removed from the chamber via the passageway;

a second tube connected to the container, the second tube being in fluid communication with the chamber in the container, the second tube transferring a positive pressure to the chamber to prevent the chamber from closing due to flexibility of the container and the vacuum created therein; and wherein a plurality of support partitions defines at least one pressurized flow path which extends between the tube and the second tube.

12. An accessory configured for detachable placement on a blade of a laryngoscope, the blade having first and second opposing major blade surfaces, the accessory comprising:

a container defining a chamber therein, the container having an upper surface and a lower surface, at least one channel is formed in an outer surface of the container such that liquid can enter the chamber;

a tube defining a passageway therethrough and connected to the container, the passageway being in fluid communication with the chamber, a padding layer comprised of absorbent material and located on the upper surface of the container;

an adhesive layer located on the lower surface of the container such that the accessory is configured to be temporarily affixed to the blade of the laryngoscope, the accessory being configured to only contact one of the first and second opposing major blade surfaces and to cover at least a portion thereof, the tube being configured to transfer a vacuum to the chamber such that liquid that enters the container, regardless of whether the liquid travels through the padding layer first, can be removed from the chamber via the passageway;

a second tube connected to the container, the second tube being in fluid communication with the chamber in the container, the second tube transferring a positive pressure to the chamber to prevent the chamber from closing due to flexibility of the container and the vacuum created therein;

wherein the second tube is positioned concentrically within the tube; and wherein a plurality of support partitions defines at least one pressurized flow path which extends between the tube and the second tube.

13. An accessory configured for detachable placement on a blade of a laryngoscope, the blade having first and second opposing major blade surfaces, the accessory comprising:

a container defining a chamber therein, the container having an upper surface and a lower surface, at least one channel is formed in an outer surface of the container such that liquid can enter the chamber;

a tube defining a passageway therethrough and connected to the container, the passageway being in fluid communication with the chamber, a padding layer comprised of absorbent material and located on the upper surface of the container;

an adhesive layer located on the lower surface of the container such that the accessory is configured to be temporarily affixed to the blade of the laryngoscope, the accessory being configured to only contact one of the first and second opposing major blade surfaces and to cover at least a portion thereof, the tube being configured to transfer a vacuum to the chamber such that liquid that enters the container, regardless of whether the liquid travels through the padding layer first, can be removed from the chamber via the passageway;

a second tube connected to the container, the second tube being in fluid communication with the chamber in the container, the second tube transferring a positive pressure to the chamber to prevent the chamber from closing due to flexibility of the container and the vacuum created therein;

wherein the tube is positioned concentrically within the second tube; and wherein a plurality of support partitions defines at least one pressurized flow path which extends between the tube and the second tube.

* * * * *